(12) United States Patent
Xu et al.

(10) Patent No.: US 11,844,503 B2
(45) Date of Patent: Dec. 19, 2023

(54) FLEXIBLE SURGICAL INSTRUMENT SYSTEM

(71) Applicant: Beijing Surgerii Robotics Company Limited, Beijing (CN)

(72) Inventors: Kai Xu, Beijing (CN); Zhengchen Dai, Beijing (CN); Shu'an Zhang, Beijing (CN); Jiangran Zhao, Beijing (CN); Huan Liu, Beijing (CN); Bo Liang, Beijing (CN); Zhixiong Yang, Beijing (CN); Zenghui Liu, Beijing (CN)

(73) Assignee: BEIJING SURGERII ROBOTICS COMPANY LIMITED, Beijing (CN)

( * ) Notice: Subject to any disclaimer, the term of this patent is extended or adjusted under 35 U.S.C. 154(b) by 1331 days.

(21) Appl. No.: 16/329,744

(22) PCT Filed: Aug. 31, 2017

(86) PCT No.: PCT/CN2017/099853
§ 371 (c)(1),
(2) Date: Feb. 28, 2019

(87) PCT Pub. No.: WO2018/041203
PCT Pub. Date: Mar. 8, 2018

(65) Prior Publication Data
US 2019/0231330 A1      Aug. 1, 2019

(30) Foreign Application Priority Data

Aug. 31, 2016   (CN) .......................... 201610795869.9
Aug. 31, 2016   (CN) .......................... 201610799235.0

(51) Int. Cl.
*A61B 17/00*  (2006.01)
*A61B 34/00*  (2016.01)
(Continued)

(52) U.S. Cl.
CPC ........ *A61B 17/00234* (2013.01); *A61B 17/00* (2013.01); *A61B 17/29* (2013.01);
(Continued)

(58) Field of Classification Search
CPC ... A61B 17/00234; A61B 17/29; A61B 34/71; A61B 1/0055; A61B 1/0057; A61B 2017/00314; A61B 2017/00323
See application file for complete search history.

(56) References Cited

U.S. PATENT DOCUMENTS

| 10,722,314 B2 | 7/2020 | Danitz et al. |
| 2006/0199999 A1 | 9/2006 | Ikeda et al. |

(Continued)

FOREIGN PATENT DOCUMENTS

| CN | 103025225 A | 4/2013 |
| CN | 103085083 A | 5/2013 |

(Continued)

OTHER PUBLICATIONS

ISA State Intellectual Property Office of the People's Republic of China, International Search Report Issued in Application No. PCT/CN2017/099853, dated Nov. 30, 2017, WIPO, 4 pages.

(Continued)

*Primary Examiner* — Tammie K Marlen
(74) *Attorney, Agent, or Firm* — McCoy Russell LLP

(57) ABSTRACT

Disclosed is a flexible surgical instrument system, comprising a flexible continuum structure consisting of a distal structure, a middle connecting body and a proximal structure linked in sequence, and further comprising a transmission driving unit linked to the proximal structure. The transmission driving unit comprises a plurality of transmission mechanisms respectively driving corresponding proximal segments. The transmission mechanisms are operable to control the direction of a bending plane of the proximal (Continued)

segments and to control the bending angle of the proximal segments in the bending plane, so as to drive the proximal segments in the proximal structure to bend or turn in any arbitrary direction, and to further drive distal segments in the distal structure linked thereto to bend or turn in the opposite direction.

17 Claims, 21 Drawing Sheets

(51) Int. Cl.
*A61B 90/50* (2016.01)
*A61B 17/29* (2006.01)
*A61B 34/30* (2016.01)
*A61B 1/005* (2006.01)

(52) U.S. Cl.
CPC .............. *A61B 34/30* (2016.02); *A61B 34/71* (2016.02); *A61B 90/50* (2016.02); *A61B 1/0055* (2013.01); *A61B 1/0057* (2013.01); *A61B 2017/00314* (2013.01); *A61B 2017/00323* (2013.01); *A61B 2017/00336* (2013.01); *A61B 2034/301* (2016.02)

(56) References Cited

U.S. PATENT DOCUMENTS

| | | | |
|---|---|---|---|
| 2011/0295242 | A1 | 12/2011 | Spivey et al. |
| 2013/0193189 | A1 | 8/2013 | Swensgard et al. |
| 2015/0352728 | A1* | 12/2015 | Wang ...................... B25J 18/06 74/490.04 |

FOREIGN PATENT DOCUMENTS

| | | | |
|---|---|---|---|
| CN | 103707322 | A | 4/2014 |
| CN | 104546048 | A | 4/2015 |
| CN | 104783846 | A | 7/2015 |
| CN | 103707322 | B | 4/2016 |
| CN | 106308934 | A | 1/2017 |
| CN | 106562806 | A | 4/2017 |
| EP | 2248483 | A1 | 11/2010 |
| EP | 2977150 | A1 | 1/2016 |
| EP | 3025830 | B1 | 3/2018 |
| JP | 2008521485 | A | 6/2008 |
| JP | 2009136684 | A | 6/2009 |
| JP | 2014531219 | A | 11/2014 |
| WO | 2009094670 | A1 | 7/2009 |
| WO | 2013158978 | A1 | 10/2013 |
| WO | 2015023853 | A1 | 2/2015 |

OTHER PUBLICATIONS

State Intellectual Property Office of People's Republic of China, Office Action and Search Report Issued in Application No. 201610795869.9, dated May 4, 2018, 10 pages.
State Intellectual Property Office of People's Republic of China, First Search Issued in Application No. 201610799235.0, dated May 16, 2018, 2 pages.
European Patent Office, Supplementary Partial European Search Report Issued in Application No. 17845505.1, dated Jun. 30, 2020, Germany, 4 pages.
European Patent Office, Extended European Search Report Issued in Application No. 17845505.1, dated Dec. 7, 2020, Germany, 11 pages.
Japanese Patent Office, Office Action Issued in Application No. 2019-531524, dated Nov. 2, 2021, 9 pages.

* cited by examiner

FLEXIBLE SURGICAL INSTRUMENT SYSTEM

CROSS REFERENCE TO RELATED APPLICATIONS

The present patent application is a U.S. national phase of Chinese International Application No. PCT/CN2017/099853 entitled "FLEXIBLE SURGICAL INSTRUMENT SYSTEM" and filed on Aug. 30, 2017. Chinese International Application No. PCT/CN2017/099853 claims priority to Chinese Patent Application No. 201610799235.0 filed on Aug. 31, 2016, and Chinese Patent Application No. 201610795869.9 filed on Aug. 31, 2016. The entire contents of each of the above-identified applications are incorporated herein by reference in their entirety for all purposes.

TECHNICAL FIELD

The present invention relates to a medical instrument, and in particular to a flexible surgical instrument system.

BACKGROUND ART

Multi-port laparoscopic minimally invasive surgery has occupied an important position in surgery because of its small wound and rapid postoperative recovery. The existing da Vinci surgical robot of the Intuitive Surgical, Inc. assists doctors to complete the multi-port laparoscopic minimally invasive surgery and has achieved great commercial success.

For the minimally invasive surgery, after the multi-port laparoscopic surgery, single-port laparoscopic surgery and natural orifice transluminal non-invasive surgery have been developed and have less trauma to the patient and higher postoperative outcomes. However, in the single-port laparoscopic surgery and the natural orifice transluminal non-invasive surgery, all surgical instruments including a visual illumination module and a surgical operating arm have access to the surgical site through a single channel, which is extremely stringent for the preparation of the surgical instruments. A distal structure of the existing surgical instrument mainly consists of multiple rods hinged in series, and is driven by a pulling force from a wire rope, so that the surgical instrument can turn at a hinge joint. Since the wire rope has to be continuously tensioned by a pulley, this driving method is difficult to further miniaturize the surgical instrument, and is also difficult to further improve the moving performance of the instrument.

Although the Intuitive Surgical, Inc. recently introduced a da Vinci Single-Site (SS-type da Vinci) surgical robot, in which the original rigid surgical instrument is modified into a semi-rigid surgical instrument and a pre-bent sleeve is additionally provided so as to improve the moving performance of the surgical instrument to a certain extent, it is impossible to fundamentally solve the problems faced by the traditional surgical instruments.

SUMMARY OF THE INVENTION

Aiming at the above problems, an object of the present invention is to provide a flexible surgical instrument system that can be better applied to a surgical robot system that passes through a natural orifice of human body or a single surgical incision and performs an operation.

In order to achieve the above objective, following technical solution is used in the invention: a flexible surgical instrument system, comprising a flexible continuum structure consisting of a distal structure, a middle connecting body and a proximal structure linked in sequence, with a proximal end of the distal structure being linked to the proximal structure via the middle connecting body, and a distal end thereof being a surgical effecting end; the distal structure consisting of at least one distal segment, each comprising a distal fixation disk and a structural backbone; and the proximal structure comprising a proximal segment each comprising a proximal fixation disk and a structural backbone, wherein the flexible surgical instrument system further comprises a transmission driving unit linked to the proximal structure; the transmission driving unit comprises one or more transmission mechanisms respectively driving the corresponding proximal segments, the transmission mechanism can convert a pair of rotary motion inputs with axes parallel to each other into a pair of rotary motion outputs with axes orthogonal to each other, wherein one of the rotary motion outputs with an axis parallel to the axes of the rotary motion input being used for controlling the direction of a bending plane of the proximal segment, and the other rotary motion output with an axis perpendicular to the axes of the rotary motion inputs being used for controlling the bending angle of the proximal segment in the bending plane, so as to drive the proximal segments in the proximal structure to bend or turn in any arbitrary direction, and to further drive the distal segments in the distal structure linked thereto to bend or turn in the opposite direction.

In a preferred embodiment, the number of the proximal segments is equal to the number of the distal segments.

In a preferred embodiment, the middle connecting body comprises a flexible surgical instrument distal plate, a channel support plate, a transmission mechanism base plate, and a structural backbone guide channel fixedly connected between the flexible surgical instrument distal plate and the transmission mechanism base plate and passing through the channel support plate; and the structural backbones on the distal segment are securely connected, in one-to-one correspondence, to or are the same as the structural backbones on the proximal segment, and one end of the structural backbone is securely connected to the proximal fixation disk, and the other end thereof passes through the structural backbone guide channel and is then securely connected to the distal fixation disk.

In a preferred embodiment, the transmission mechanism is a gear transmission mechanism comprising a driving gear transmission mechanism, a planetary gear transmission mechanism and an ocsillation motion transmission mechanism, wherein the driving gear transmission mechanism transmits power from the outside to the planetary gear transmission mechanism, and the planetary gear transmission mechanism and the ocsillation motion transmission mechanism can convert a pair of rotary motion inputs with axes parallel to each other into a pair of the rotary motion outputs with axes orthogonal to each other, the planetary gear transmission mechanism uses the rotary motion output with an axis parallel to the axes of the rotary motion inputs for controlling the direction of a bending plane of the proximal segment, and the ocsillation motion transmission mechanism uses the rotary motion output with an axis perpendicular to the axes of the rotary motion input for controlling the bending angle of the proximal segment in the bending plane.

In a preferred embodiment, the driving gear transmission mechanism comprises two driving gears respectively securely connected to one end of two driving shafts, and the other end of the driving shafts are securely connected to a first coupling male connecter; and the two driving gears respectively mesh with a first driven ring gear and a second driven ring gear through an idle gear and drive same to rotate, and the second driven ring gear has teeth on both the inner and outer sides, with the teeth on the outer side meshing with the idle gear.

In a preferred embodiment, the planetary gear transmission mechanism comprises: a planetary gear support plate and a support base securely connected to the first driven ring gear, a planetary gear transmission shaft with one end rotatably disposed on the planetary gear support plate, a planetary gear securely connected to the planetary gear transmission shaft, and a planetary bevel gear securely connected to the other end of the planetary gear transmission shaft, wherein the second driven ring gear is rotatably disposed on the planetary gear support plate, and the teeth on the inner side of the second driven ring gear mesh with the planetary gear; and the support base is simultaneously rotatably connected to the transmission mechanism base plate.

In a preferred embodiment, the ocsillation motion transmission mechanism comprises: an oscillating shaft support securely connected to the support base, an oscillating shaft rotatably disposed on the oscillating shaft support, a web plate securely connected to the oscillating shaft, an bevel gear for oscillation and a guide column securely connected to the web plate, and a guide sleeve slidably connected to the guide column, wherein the bevel gear for oscillation is a partial bevel gear, with the oscillating axis of the bevel gear for oscillation coinciding with the axis of the oscillating shaft, and the bevel gear for oscillation meshes with the planetary bevel gear; and the guide sleeve is securely connected to a proximal segment fixation disk driving plate, while the proximal fixation disk is securely connected to the proximal segment fixation disk driving plate.

In a preferred embodiment, the transmission driving unit further comprises a surgical end effector driving mechanism, while the distal end of the distal structure is provided with a surgical end effector; and the surgical end effector driving mechanism comprises: a flexible surgical instrument bottom plate, a threaded rod rotatably supported between the channel support plate and the flexible surgical instrument bottom plate, a first coupling male connecter securely connected to one end of the threaded rod, a nut threadedly fitted with the threaded rod, a guide rod securely connected between the transmission mechanism base plate and the channel support plate and slidably connected to the nut, and a surgical end effector control line with one end securely connected to the surgical end effector and the other end passing through the distal structure and securely connected to the nut.

In a preferred embodiment, the flexible surgical instrument system further comprises a motor driving unit linked to the flexible surgical instrument, the motor driving unit comprising: a plurality of first motors securely connected to a motor fixation plate, a motor driving unit housing rotatably connected to the periphery of the motor fixation plate, an inner ring gear securely connected to an end surface of the motor driving unit housing, a gear securely connected to one of the first motor output shafts, and a second coupling male connecter securely connected to the other first motor output shaft, wherein the first motor connected to the gear drives the gear to rotate, and further drives all the structures, other than the motor driving unit housing and the inner ring gear, in the motor driving unit to rotate as a whole around the axis of the inner ring gear so as to achieve control over the roll angle of the distal structure.

In a preferred embodiment, the flexible surgical instrument is connected to the motor driving unit via a sterile barrier, wherein the sterile barrier comprises a sterile barrier cover and a sterile barrier support plate, and the sterile barrier support plate is rotatably provided with a plurality of coupling female connecters that can be quickly coupled with the first coupling male connecter and the second coupling male connecter respectively; a motor driving unit connecting screw is provided on the sterile barrier support plate, and correspondingly, a sterile barrier connecting base is provided on the motor fixation plate, the sterile barrier connecting base being connected to the motor driving unit connecting screw so that the sterile barrier is fixedly connected to the motor fixation plate and can transmit an overall movement; and a sterile membrane for isolating a sterilizable part from an unsterilized part is securely connected on the sterile barrier cover.

In a preferred embodiment, the flexible surgical instrument system further comprises a linear module that comprises: a support body with a linear sliding groove, a lead screw rotatably disposed on the support body, a sliding block threadedly fitted with the lead screw and slidably disposed in the linear sliding groove, and a second motor securely connected to the support body, wherein the sliding block is securely connected to the motor driving unit housing, and the second motor output shaft is securely connected to the lead screw.

In a preferred embodiment, the transmission mechanism is a cam transmission mechanism comprising two driving gears respectively securely connected to one end of two driving shafts, and the other end of the driving shafts are coaxially and securely connected to the first coupling male connecter; the driving gears respectively mesh with a first driven ring gear and a second driven ring gear and drive same to rotate; the first driven ring gear is securely connected to a cam, and the cam is rotatably connected to the transmission mechanism base plate; the second driven ring gear is integrally and securely connected to a transmission shaft, a rotary driving plate and a support plate, the support plate is rotatably connected to the transmission mechanism base plate, and the cam is rotatably connected to the rotary driving plate; and the cam transmission mechanism further comprises a planar linkage mechanism with one end securely connected to a sliding block, and the sliding block is axially slidably connected to the transmission shaft and can transmit a circumferential rotary motion; a number of rollers are securely connected to the sliding block, and the rollers match spiral cam slots on the cam and can generate a push-pull force in the axial direction of the transmission shaft; and the other end of the planar linkage mechanism is slidably connected to a proximal fixation disk driving plate, while the proximal fixation disk is securely connected to the proximal fixation disk driving plate.

In a preferred embodiment, the planar linkage mechanism consists of a push rod, a connecting rod and a rocking bar, the push rod being slidably connected to the support plate, with one end thereof being securely connected to the sliding block and the other end thereof passing through the support plate and being rotatably connected to one end of the connecting rod, the other end of the connecting rod being rotatably connected to the rocking bar that is rotatably fixed to the transmission shaft, and the rocking bar being slidably connected to the proximal fixation disk driving plate.

In a preferred embodiment, the distal segment further comprises a plurality of distal spacer disks distributed therein at intervals, and a plurality of structural backbones of the distal segment pass through structural backbone passing holes distributed in the distal spacer disks, with the tail ends thereof fixed onto the distal fixation disk; and the proximal segment further comprises a plurality of proximal spacer disks distributed therein at intervals, and a proximal segment fixation base plate securely connected to the transmission mechanism base plate, and a plurality of structural backbones of the proximal segment have one end thereof fixed onto the proximal fixation disks and the other end sequentially pass through structural backbone passing holes distributed in the proximal spacer disks and are then securely connected, in one-to-one correspondence, to or are the same as the structural backbones of the distal segment.

In a preferred embodiment, the structural backbone of the distal segment and/or the structural backbone of the proximal segment are/is an elastic thin rod or thin tube made of a nickel titanium alloy or stainless steel; in the case of using the plurality of distal segments or the plurality of proximal segments, if the structural backbone of the former distal segment or the structural backbone of the former proximal segment uses an elastic thin tube, the structural backbone of the next distal segment or the structural backbone of the next proximal segment can pass through the elastic thin tube or directly pass through the structural backbone passing holes in the distal spacer disks or in the proximal spacer disks; and the number of structural backbones of each of the distal segments or the proximal segments is three or more.

In a preferred embodiment, the distal structure is externally covered with an envelope, and an outer sheath and a trocar are provided outside the envelope.

The present invention adopts the above technical solutions, and has the following advantages: 1. in the present invention, a flexible continuum structure comprising a proximal structure, a middle connecting body and a distal structure is used as the main body, and is cooperated with a transmission driving unit, wherein a distal structure is linked to a proximal structure via a middle connecting body, the transmission driving unit is linked to the proximal structure, and when the transmission driving unit drives proximal segments in the proximal structure to bend or turn in any arbitrary direction, the distal structure correspondingly bends or turns in the opposite direction, so as to implement the bending motion in any arbitrary direction of the flexible surgical arm formed of the distal structure and an envelope. 2. In the present invention, in the proximal structure, the middle connecting body and the distal structure, a redundant arrangement of structural backbones (more than three) is used, which can improve the safety, reliability and load capacity of the flexible surgical instrument system. 3. In the present invention, the sterile barrier can be quickly connected to the flexible surgical instrument at one end and quickly connected to a motor driving unit at the other end, so as to effectively isolate the sterilized flexible surgical instrument from the remaining unsterilized parts of the system, thereby ensuring the implementation of the clinical operation. 4. In the present invention, the flexible surgical instrument is provided with a gear transmission mechanism that can convert a pair of rotary motion inputs with axes parallel to each other into a pair of rotary motion outputs with axes orthogonal to each other, in which one rotary motion output (implemented by a first driving mode) with the axis parallel to the axes of the rotary motion inputs is used for controlling the direction of a bending plane of the proximal segments, and the other rotary motion output (implemented by a second driving mode) with the axis perpendicular to the axes of the rotary motion inputs is used for controlling the bending angle of the proximal segments in the bending plane, so as to finally drive one of the proximal segments in the proximal structure to bend or turn in any arbitrary direction in a small space by a group of gear transmission mechanisms. 5. In the present invention, the front end of the distal structure is provided with a surgical end effector, and a surgical end effector control line passes through the flexible continuum structure and is connected to a surgical end effector driving mechanism in the flexible surgical instrument, so as to achieve motion control over the surgical end effector. 6. In the present invention, a motor driving unit housing is further provided, an inner ring gear is fixedly connected at an end surface of the motor driving unit housing, and the remaining structure in the motor driving unit can rotate relative to the motor driving unit housing, wherein the motor output shaft is fixedly connected to a gear that meshes with the inner ring gear, and therefore the motor can drive the parts except the motor driving unit housing and the inner ring gear to rotate as a whole so that the flexible surgical arm has an overall rotational freedom. 7. The invention is further provided with a linear module that is fixedly connected to the motor driving unit housing and can drive the motor driving unit, the sterile barrier and the flexible surgical instrument to perform linear movement so that the flexible surgical arm also has a linear feed freedom. 8. The present invention can be applied to the single-port laparoscopic surgery, and can also be applied to the natural orifice transluminal non-invasive surgery.

DETAILED DESCRIPTION OF EMBODIMENTS

The preferred embodiments of the present invention will be described below in detail with reference to the accompanying drawings so as to more clearly understand the objects, features and advantages of the present invention. It should be understood that the embodiments shown in the accompanying drawings are not intended to limit the scope of the present invention, but are intended only to illustrate the essential spirit of the technical solutions of the present invention.

Figure 1:
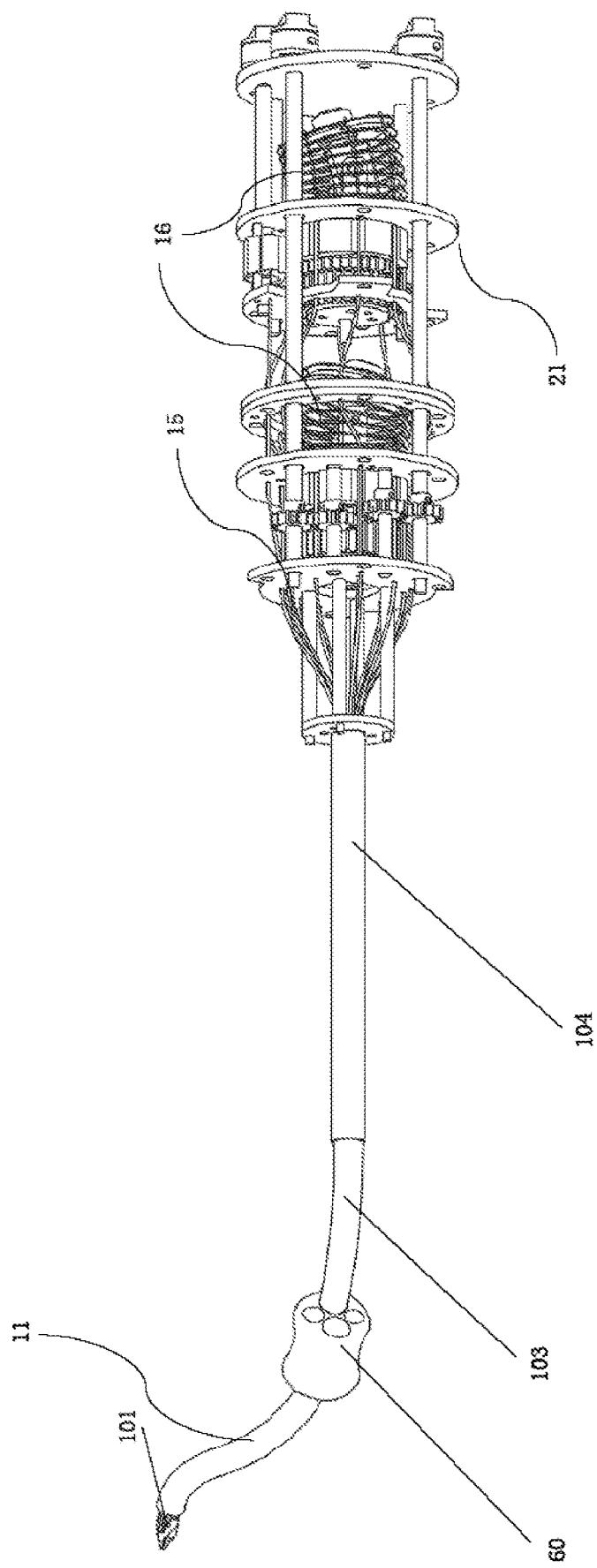
FIG. 1 is an overall structural schematic diagram of a flexible surgical instrument system according to a first embodiment of the present invention.

FIG. 1 illustrates a flexible surgical instrument system 10 provided according to this embodiment, the flexible surgical instrument system comprising a flexible continuum structure consisting of a distal structure 11, a proximal structure 16 and a middle connecting body 15, and a transmission driving unit 21 linked to the flexible continuum structure. Here, a proximal end of the distal structure 11 is linked to the proximal structure 16 via the middle connecting body 15, and a distal end is a surgical effecting end. The transmission driving unit 21 is linked to the proximal structure 16, and when the transmission driving unit 21 drives the proximal structure 16 to bend or turn in any arbitrary direction, the distal structure 11 correspondingly bends or turns in the opposite direction.

Figure 2:
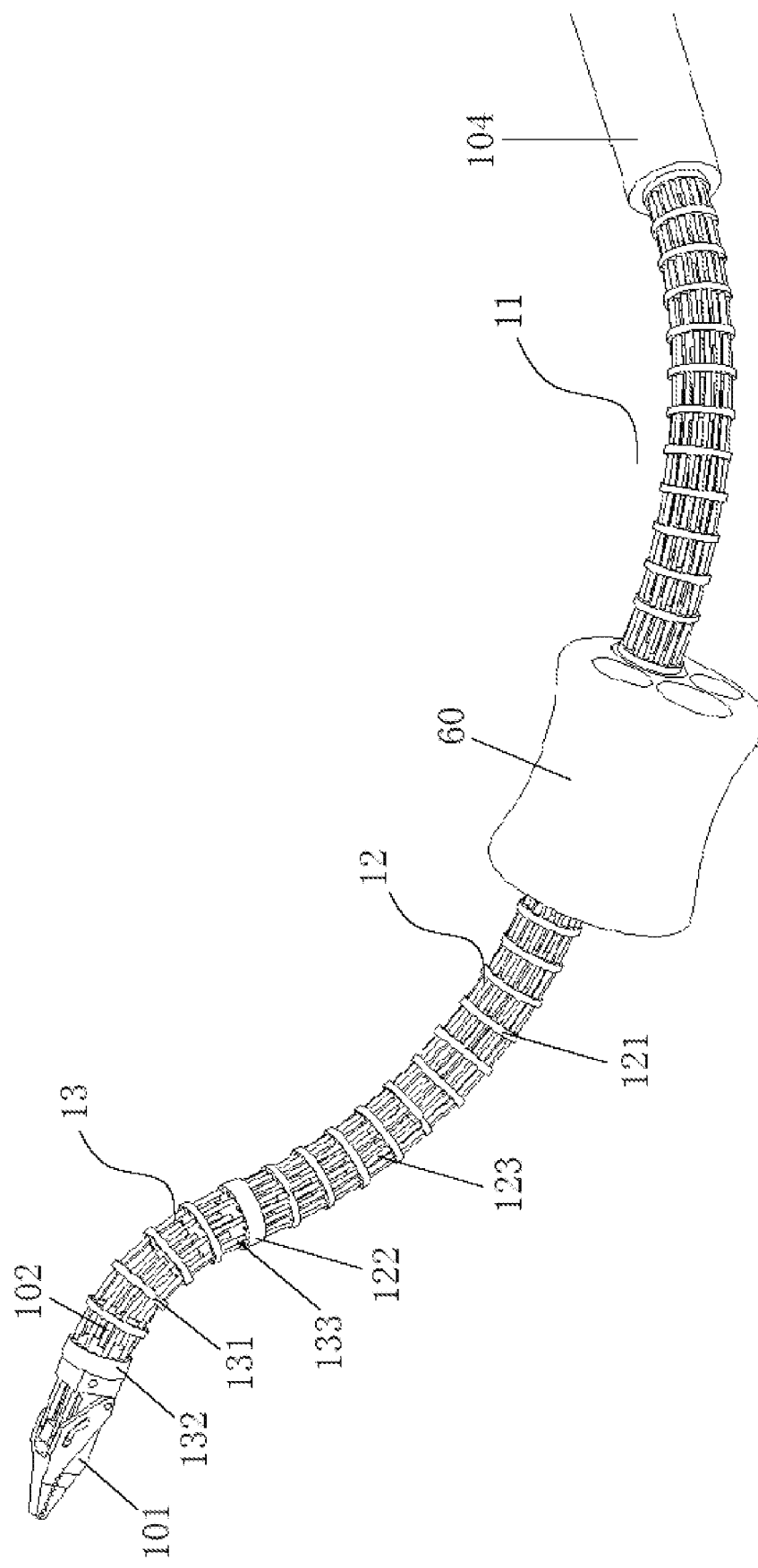
FIG. 2 is a structural schematic diagram of a distal structure in FIG. 1.

As shown in FIG. 2, the distal structure 11 comprises a surgical end effector 101, a first distal segment 12 and a second distal segment 13. Here, the first distal segment 12 comprises first distal spacer disks 121, a first distal fixation disk 122 and first segment structural backbones 123. A number of first distal spacer disks 121 are distributed in the first distal segment 12 at intervals, and functions to prevent the first segment structural backbones 123 from losing stability when being pushed. A plurality of the first segment structural backbones 123 pass through structural backbone passing holes distributed in the first distal spacer disks 121, with the tail ends thereof fixed onto the first distal fixation disk 122. Similarly, the second distal segment 13 comprises second distal spacer disks 131, a second distal fixation disk 132 and second segment structural backbones 133. A number of second distal spacer disks 131 are distributed in the second distal segment 13 at intervals, and functions to prevent the second segment structural backbones 133 from losing stability when being pushed. A plurality of the second segment structural backbones 133 pass through structural backbone passing holes distributed in the second distal spacer disks 131, with the tail ends thereof fixed onto the second distal fixation disk 132. It should be noted that the first segment structural backbones 123 and the second segment structural backbones 133 should respectively be three or more in number.

Figure 3:
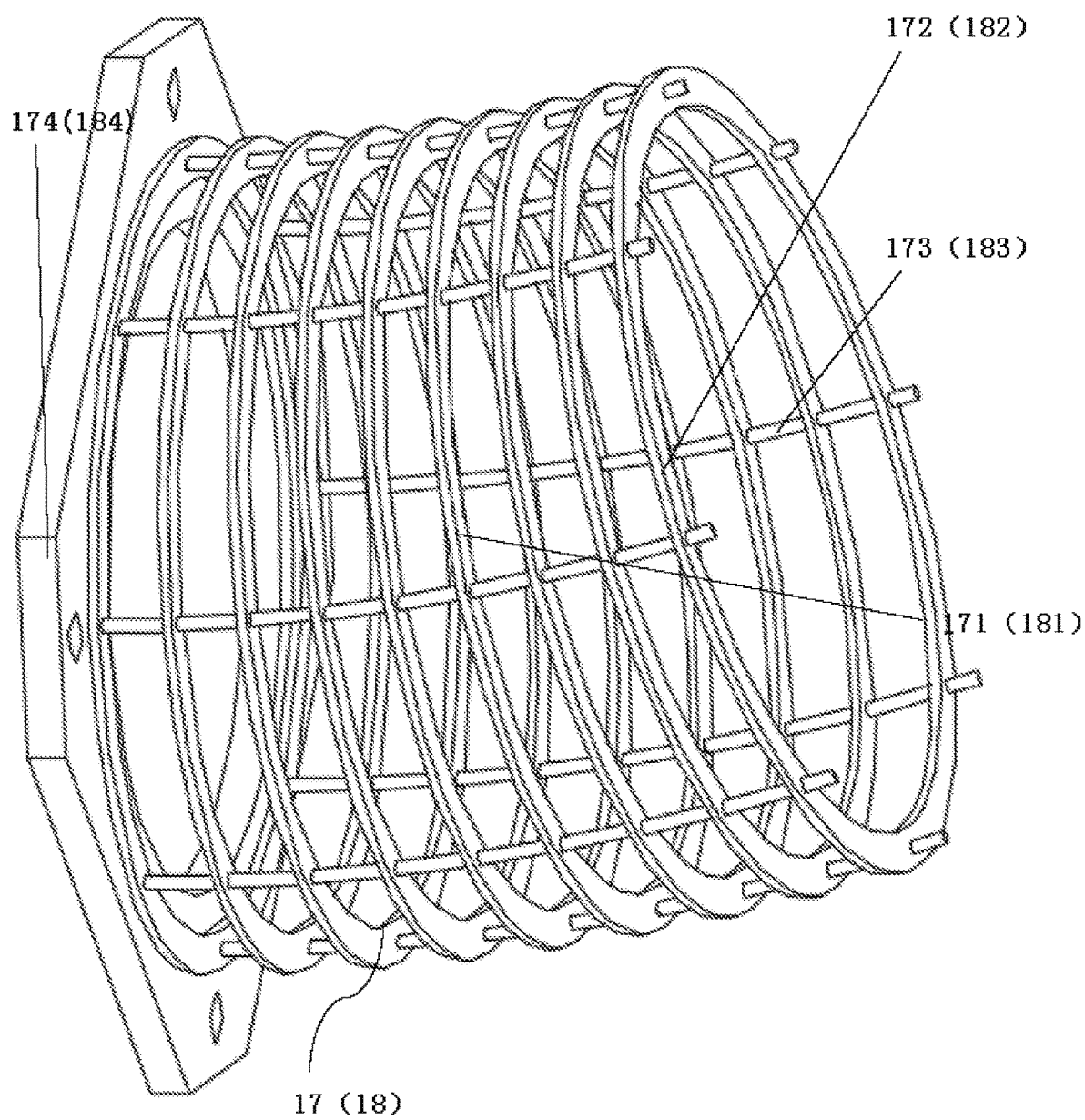
FIG. 3 is a structural schematic diagram of a proximal segment in FIG. 1.

As shown in FIGS. 1 and 3, the proximal structure 16 comprises a first proximal segment 17 and a second proximal segment 18 with identical structures. The first proximal segment 17 comprises first proximal spacer disks 171, a first proximal fixation disk 172, first segment structural backbones 173 and a first proximal segment fixation base plate 174, and a number of the first proximal spacer disks 171 are distributed in the first proximal segment 17 at intervals and function to prevent the first segment structural backbones 173 from losing stability when being pushed. Similarly, the second proximal segment 18 comprises second proximal spacer disks 181, a second proximal fixation disk 182, second segment structural backbones 183 and a second proximal segment fixation base plate 184, and a number of the second proximal spacer disks 181 are distributed in the second proximal segment 18 at intervals and function to prevent the second segment structural backbones 183 from losing stability when being pushed. The first segment structural backbones 173 on the first proximal segment 17 are securely connected, in one-to-one correspondence, to or are the same as the first segment structural backbones 123 on the first distal segment 12; and the second segment structural backbones 183 on the second proximal segment 18 are securely connected, in one-to-one correspondence, to or are the same as the second segment structural backbones 133 on the second distal segment 13. It should be noted that the first segment structural backbones 173 and the second segment structural backbones 183 should be consistent in number with the first segment structural backbones 123 and the second segment structural backbone 133, respectively.

Figure 4:
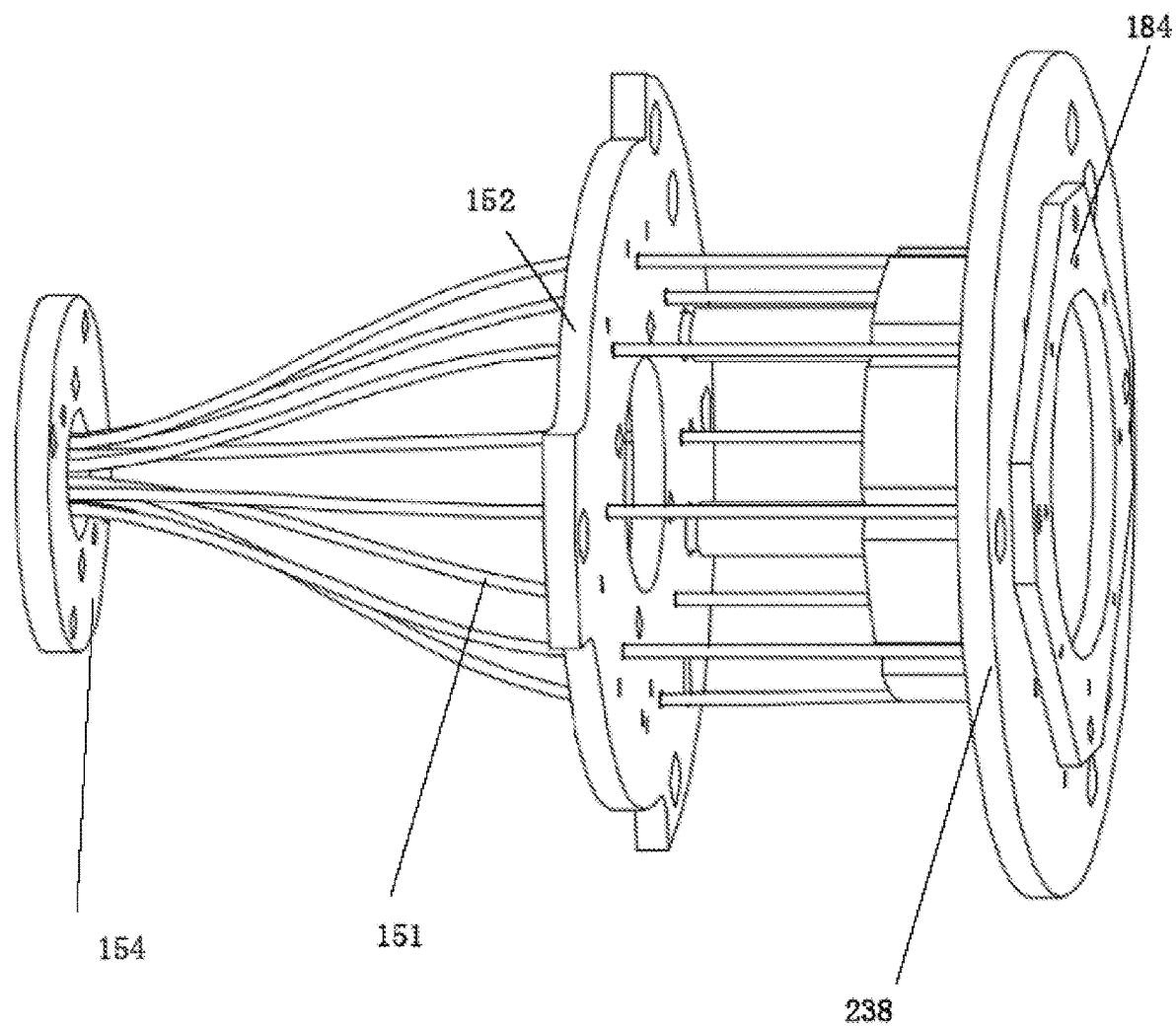
FIG. 4 is a structural schematic diagram of a middle connecting body in FIG. 1.

As shown in FIG. 4, the middle connecting body 15 comprises a distal channel fixation plate 154, a channel support plate 152 and a gear transmission mechanism base plate 238 disposed in sequence at intervals, and structural backbone guide channels 151 fixedly connected between the distal channel fixation plate 154 and the gear transmission mechanism base plate 238 and passing through the channel support plate 152. It should be noted that the channel support plate 152 and the gear transmission mechanism base plate 238 may be provided as one group, or may be provided as multiple groups (for example, two groups are provided in FIG. 5) disposed at intervals, and the number of group of the channel support plate 152 and the gear transmission mechanism base plate 238 is consistent with the number of the gear transmission mechanisms 22 in the transmission driving unit 21. One end of the first segment structural backbone 173 (123) is securely connected to the first proximal fixation disk 172, and the other end passes through the first proximal spacer disks 171, the structural backbone guide channel 151 and the first distal spacer disks 121 in sequence and is then securely connected to the first distal fixation disk 122. One end of the second segment structural backbone 183 (133) is securely connected to the second proximal fixation disk 182, and the other end passes through the second proximal spacer disks 181, the structural backbone guide channel 151, the first distal segment 12 and the second distal spacer disks 131 in sequence and is then securely connected to the second distal fixation disk 132. The structural backbone guide channel 151 functions to maintain the shape of the structural backbone under a pushing or pulling force.

In a preferred embodiment, the above structural backbones in the distal structure 11 and/or the structural backbones in the proximal structure 16 may be elastic thin rods or thin tubes, and are made of a material such as nickel titanium alloy or stainless steel. Meanwhile, the number of the above distal segments in the distal structure 11 and the proximal segments in the proximal structure 16 may be one or more than two. However, the number of the distal segments in the distal structure 11 is consistent with the number of the proximal segments in the proximal structure 16 all the time. In the case of using a plurality of distal segments or proximal segments, if the structural backbone of the former distal segment or proximal segment uses an elastic thin tube, the structural backbone of the next distal segment or proximal segment can pass through the elastic thin tube or directly passes through structural backbone passing holes in the distal spacer disks or the proximal spacer disks, which implements further miniaturization without changing the relative motion relationship in the distal structure 11 or the proximal structure 16. Moreover, the relative arrangement of the proximal segments in the proximal structure 16 can be series connection, nested arrangement, or independent arrangement (as shown in FIG. 1), etc.

As shown in FIGS. 5 to 8, the transmission driving unit 21 comprises two gear transmission mechanisms 22 (only by way of example, and not limited thereto) correspondingly driving the first proximal segment 17 and the second proximal segment 18, respectively. The gear transmission mechanism 22 comprises two driving gears 221 securely connected to one end of the two driving shafts 213, respectively, and the other end of the two driving shafts 213 are coaxially and securely connected to the two coupling male connecters 212, respectively. The two driving gears 221 respectively mesh with a first driven ring gear 223 and a second driven ring gear 224 by an idle gear 222 and drive the rotation thereof. The first driven ring gear 223 is securely connected to a planetary gear support plate 227 and a support base 228, the support base 228 is securely connected to an oscillating shaft support 234, and the support base 228 is rotatably connected to the gear transmission mechanism base plate 238 that is securely connected to the first proximal segment fixation base plate 174 or the second proximal segment fixation base plate 175. The second driven ring gear 224 is rotatably disposed on the planetary gear support plate 227, and is provided with teeth on both the inner and outer sides, with the teeth on the outer side meshing with the idle gear 222, and the teeth on the inner side meshing with and driving a planetary gear 225 that is securely connected to a planetary gear transmission shaft 226. The planetary gear transmission shaft 226 is rotatably disposed on the planetary gear support plate 227, and one end of the planetary gear transmission shaft 226 is securely connected to a planetary bevel gear 229. An bevel gear for oscillation 231 is a partial bevel gear and is securely connected to a web plate 232, the web plate 232 is securely connected to an oscillating shaft 233, and the oscillating axis of the bevel gear for oscillation 231 coincides with the axis of the oscillating shaft 233. The oscillating shaft 233 is rotatably disposed on the oscillating shaft support 234, and the bevel gear for oscillation 231 meshes with the planetary bevel gear 229 to transmit the motion. The web plate 232 is securely connected to the guide column 235, the guide column 235 is slidably connected to a guide sleeve 236, the guide sleeve 236 is securely connected to a proximal segment fixation disk driving plate 237, and both the first proximal fixation disk 172 and the second proximal fixation disk 182 are securely connected to one proximal fixation disk driving plate 237.

When the first driven ring gear 223 rotates, the planetary gear support plate 227 and the support base 228 securely connected to the first driven ring gear 223 rotate, together with the oscillating shaft support 234, around the axis of the first driven ring gear 223, and further drive the planetary gear transmission shaft 226, the planetary gear 225, the planetary bevel gear 229, the bevel gear for oscillation 231, the oscillating shaft 233, the web plate 232, the guide column 235 and other structures to rotate around the axis of the first driven ring gear 223, so as to directly control the direction of the bending planes of the first proximal segment 17 and the second proximal segment 18; and when the second driven ring gear 224 rotates, the teeth on the inner side thereof mesh with the planetary gear 225, the bending angle difference between the second driven ring gear 224 and the first driven ring gear 223 drives the planetary gear 225, the planetary gear transmission shaft 226 and the planetary bevel gear 229 to rotate around their own axes, and by means of the planetary bevel gear 229 meshing with the bevel gear for oscillation 231, the bevel gear for oscillation 231 and the web plate 232 are driven to oscillate around the axis of the oscillating shaft 233 in a certain range to drive the guide column 235 to slide along the guide sleeve 236 and finally drive the proximal segment fixation disk driving plate 237 to bend or turn, so as to directly control the bending angle of the first proximal segment 17 and the second proximal segment 18 in the above bending plane, without changing the lengths of the first proximal segment 17 and the second proximal segment 18, so that the first proximal segment 17 and the second proximal segment 18 bend or turn in an approximately circular arc shape.

In the first driving mode, when the first driven ring gear 223 and the second driven ring gear 224 are driven to rotate in the same direction at the same angular speed, no relative rotation exists between the planetary gear 225 and the second driven ring gear 224, so that the planetary gear 225, the planetary gear transmission shaft 226 and the planetary bevel gear 229 have no rotary motion relative to their own axes, so as to remain the bending angle of the first proximal segment 17 and the second proximal segment 18 unchanged in the respective bending planes, only with the change in the direction of the oscillating plane of the bevel gear for oscillation 231, that is, the direction of the bending plane of the proximal segment fixation disk driving plate 237, finally implementing the adjustment for the direction of the bending planes of the first proximal segment 17 and the second proximal segment 18 without changing the bending angles of the first proximal segment 17 and the second proximal segment 18 in the above bending planes; and in the second driving mode, the first driven ring gear 223 is stationary, the second driven ring gear 224 is driven, and at the moment the planetary gear support plate 227 and the parts securely connected thereto are all stationary relative to the gear transmission mechanism base plate 238, and the bending angles of the first proximal segment 17 and the second proximal segment 18 only change in the bending planes, with the direction of the bending planes thereof unchanged. Combining the first driving mode with the second driving mode, cooperative control for the direction of the bending plane and for the bending angle in the bending plane of the first proximal segment 17 and the second proximal segment 18 can be implemented. When the first proximal segment 17 bends or turns in a certain direction, the first distal segment 12 will bend or turn in the opposite direction in a certain proportional relationship (determined by the distribution radius of the first segment structural backbone 123 (173) together); and similarly, when the second proximal segment 18 bends or turns in a certain direction, the second distal segment 13 will bend or turn in the opposite direction in a certain proportional relationship (determined by the distribution radius of the second segment structural backbone 133 (183) together).

Figure 5:
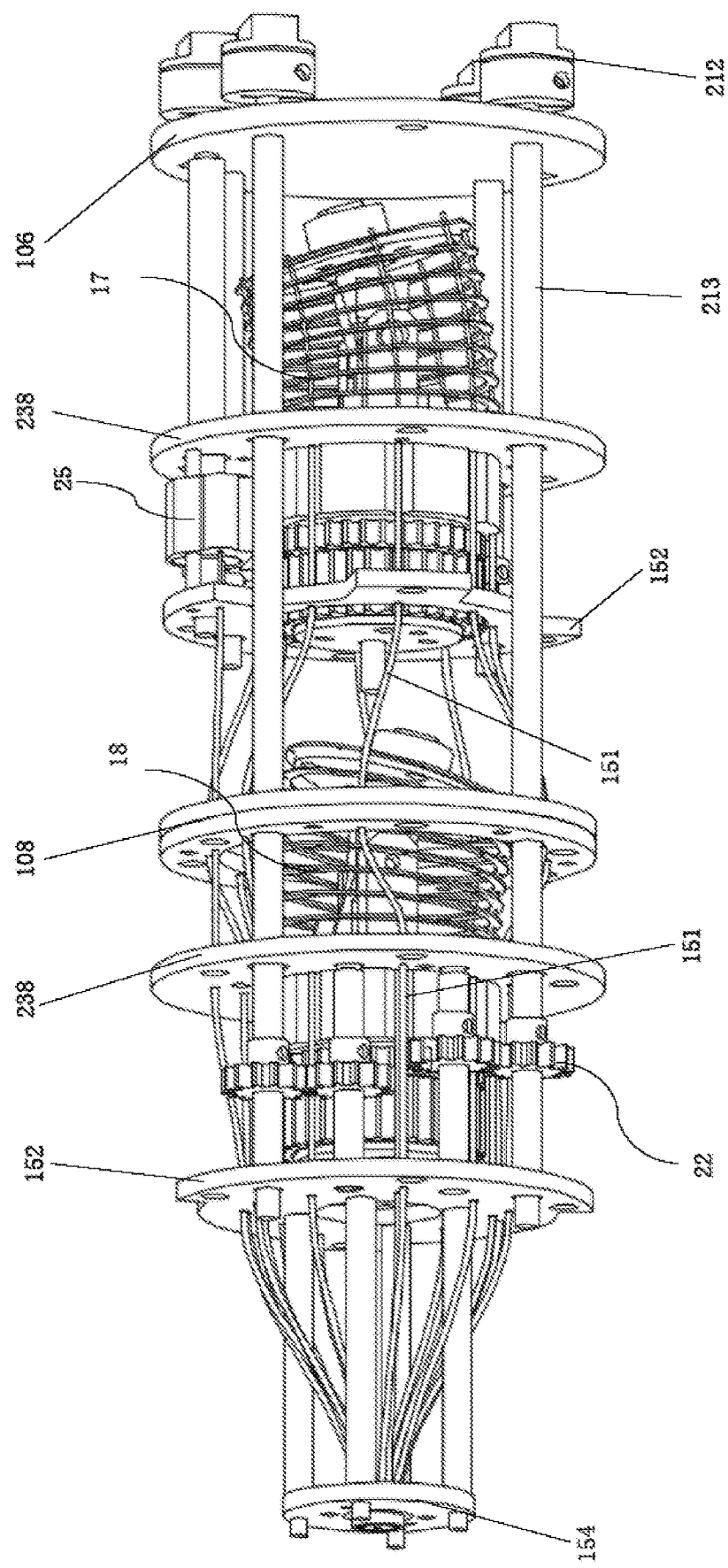
FIG. 5 is a structural schematic diagram of a transmission driving unit in FIG. 1.
Figure 6:
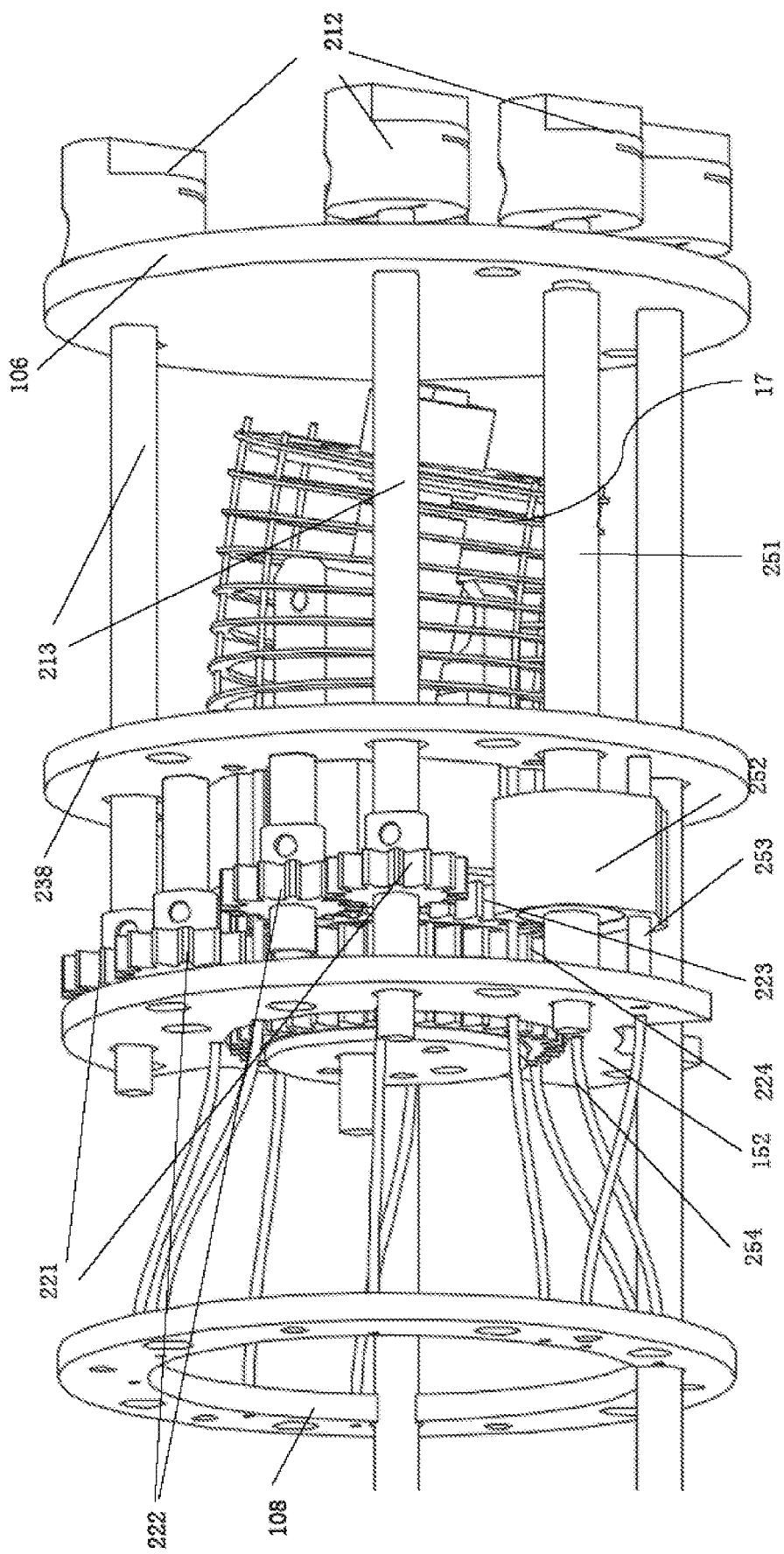
FIG. 6 is a structural schematic diagram of a gear transmission mechanism and a surgical end effector driving mechanism in FIG. 1.
Figure 7:
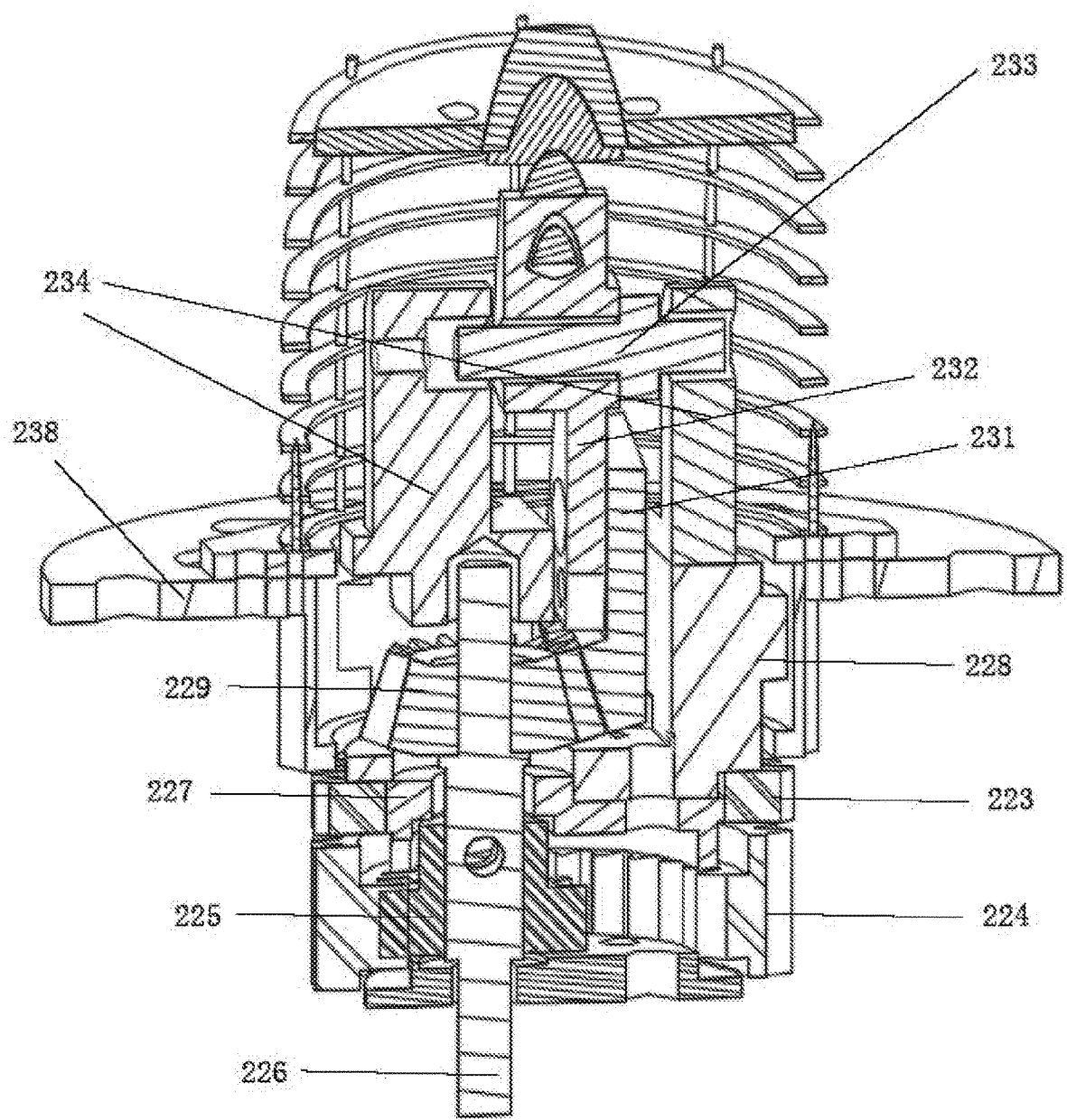
FIG. 7 is a cross-sectional view of the gear transmission mechanism in FIG. 1.
Figure 8:
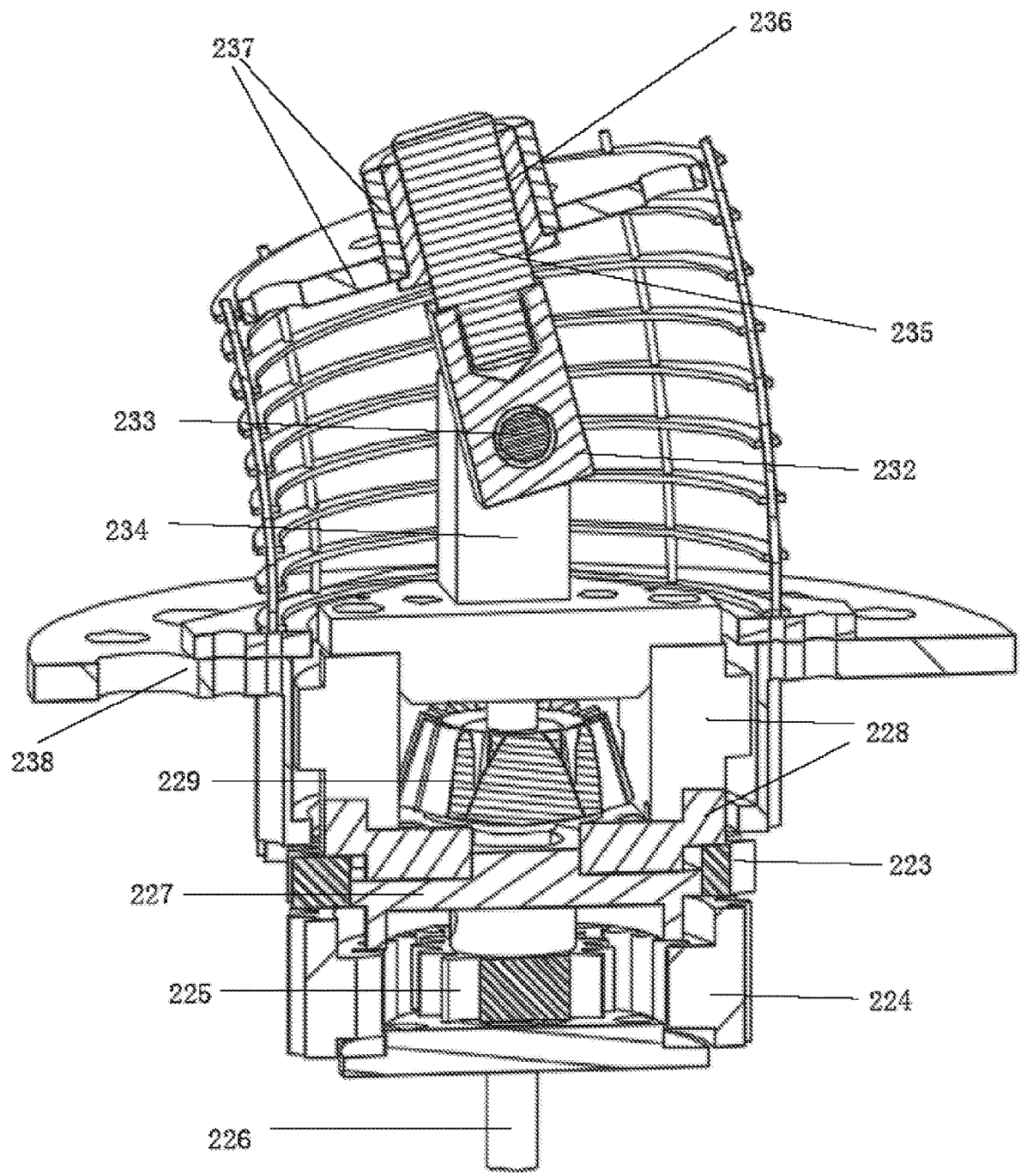
FIG. 8 is a cross-sectional view of the gear transmission mechanism in FIG. 1 in another direction.

In a preferred embodiment, the distal end of the distal structure 11 is provided with a surgical end effector 101 (as shown in FIGS. 1 and 2), one end of a surgical end effector control line 102 is fixedly connected to the surgical end effector 101, and the other end thereof passes through the distal structure 11 and is connected to a surgical end effector driving mechanism 25 (as shown in FIGS. 5 and 6) at a tail end of the transmission driving unit 21, so that the surgical end effector driving mechanism 25 implements the motion control for the surgical end effector 101 (such as a surgical clamp) by physically pushing and pulling the surgical end effector control line 102. It will be understood by those skilled in the art that the surgical end effector control line 102 can also transmit energy, such as electric energy, ultrasonic vibration, etc., to an electrosurgical surgical end effector 101 (such as an electric knife, an ultrasonic knife, etc.) so as to implement the specific surgical function of the surgical end effector 101. The surgical end effector driving mechanism 25 comprises a threaded rod 251 and a nut 252. Here, the threaded rod 251 is rotatably supported between the channel support plate 152 and a flexible surgical instrument bottom plate 106, one end of the threaded rod 251 is coaxially and securely connected to another coupling male connecter 212, the threaded rod 251 is threadedly fitted with the nut 252, and a guide rod 253 is securely connected between the gear transmission mechanism base plate 238 and the channel support plate 152 and is slidably connected to the nut 252. The threaded rod 251 is driven to rotate by the power from the outside by means of the coupling male connecter 212, so that the nut 252 is guided by the guide rod 253 to move back and forth in linear motion to push and pull the surgical end effector control line 102 which has one end securely connected to the nut 252, so as to finally implement the motion control for the surgical end effector 101.

Figure 9:
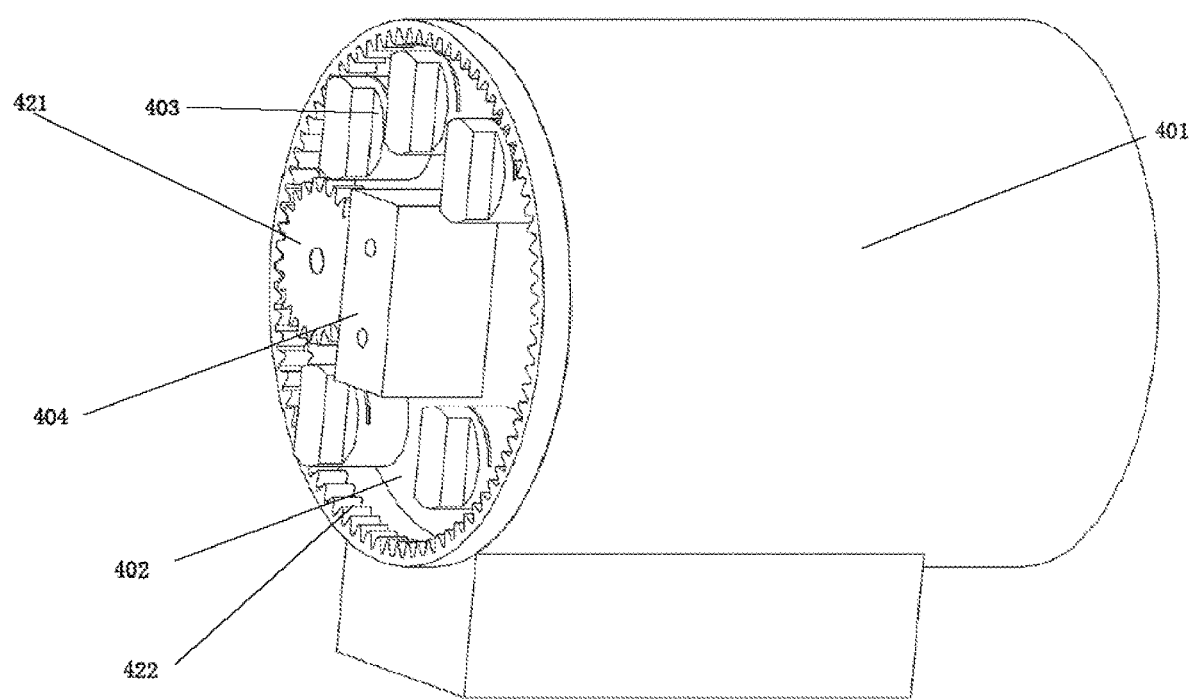
FIG. 9 is a structural schematic diagram of a motor driving unit in FIG. 1.
Figure 10:
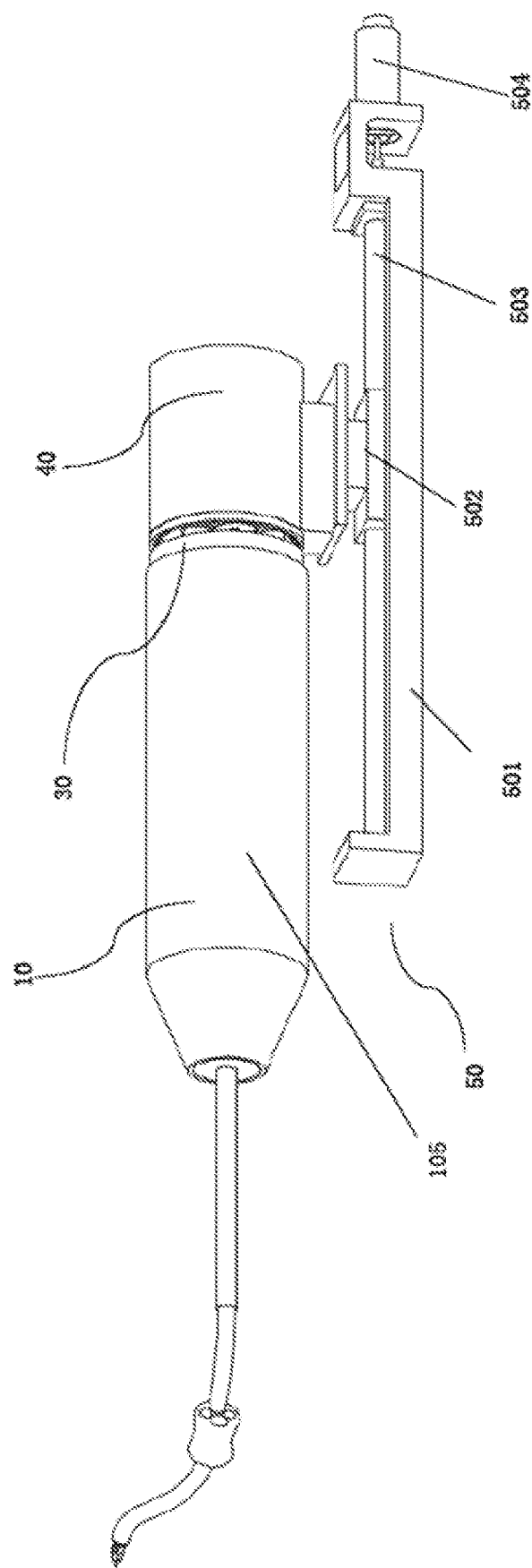
FIG. 10 is a schematic diagram of a structure installed with a sterile barrier, a motor driving unit and a linear module of the present invention.

In a preferred embodiment, as shown in FIGS. 9 and 10, the present invention further comprises a motor driving unit 40 linked to the flexible surgical instrument 10, and the motor driving unit 40 comprises a motor driving unit housing 401, a motor fixation plate 402, a gear 421 and an inner ring gear 422. Here, the motor driving unit housing 401 is located at the periphery of the motor fixation plate 402, an end surface of the motor driving unit housing 401 is securely connected to the inner ring gear 422, and the motor fixation plate 402 is rotatably connected to the motor driving unit housing 401. A plurality of motors (six motors in this embodiment) are securely connected to the motor fixation plate 402, in which the output shaft of one of the motors is securely connected to the gear 421, the output shafts of the remaining motors are securely connected to coupling male connecters 403, and the gear 421 meshes with the inner ring gear 422. The motor connected to the gear 421 can drive the gear 421 to rotate, and drive all the structures, other than the motor driving unit housing 401 and the inner ring gear 422, in the motor driving unit 40 to rotate as a whole around the axis of the inner ring gear 422 so as to achieve control over the roll angle of the distal structure 11 and the surgical end effector 101.

Figure 11:
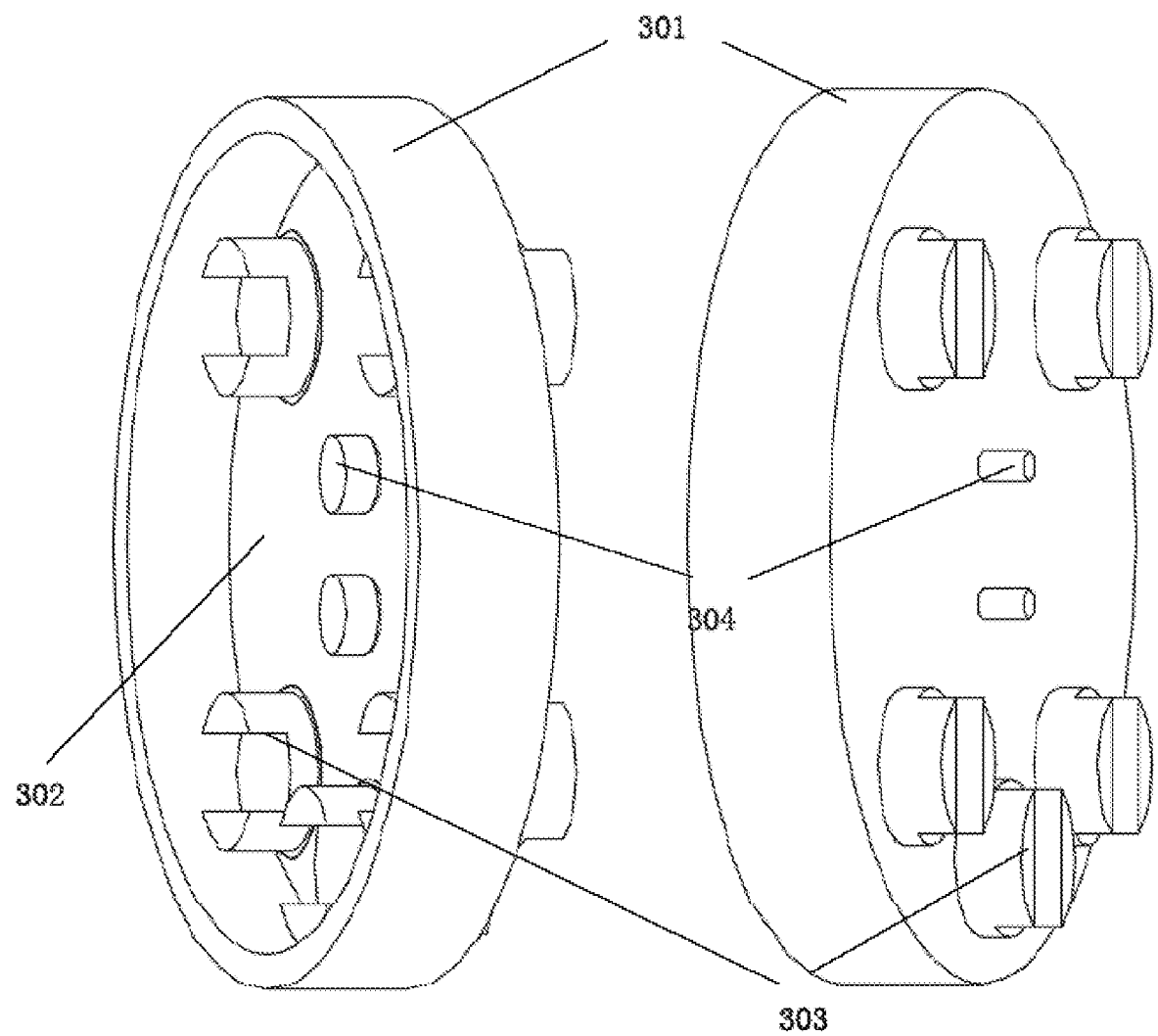
FIG. 11 is a structural schematic diagram of the sterile barrier of the present invention.

In a preferred embodiment, as shown in FIGS. 10 and 11, the flexible surgical instrument 10 can be quickly connected to the motor driving unit 40 via a sterile barrier 30, the sterile barrier 30 comprises a sterile barrier cover 301 and a sterile barrier support plate 302, and a plurality of coupling female connecters 303 that can be respectively quickly coupled with the coupling male connecters 212 and 403 are rotatably disposed on the sterile barrier support plate 302. A motor driving unit connecting screw 304 is provided on the sterile barrier support plate 302, and correspondingly, a sterile barrier connecting base 404 (as shown in FIG. 9) is provided on the motor fixation plate 402, and the sterile barrier connecting base 404 can be quickly connected to the motor driving unit connecting screw 304, so that the sterile barrier 30 can be fixedly connected to the motor fixation plate 402 and can transmit an overall movement. A sterile membrane (not shown in the figure) is securely connected on the sterile barrier cover 301 to isolate the sterilizable parts (such as the flexible surgical instrument 10 and other parts in front of the sterile barrier 30) from the unsterilized parts (such as the motor driving unit 40, a linear module 50 and other parts behind the sterile barrier 30) to ensure the clinical practicability of the surgery.

In a preferred embodiment, as shown in FIG. 10, the present invention further comprises a linear module 50 (the linear module 50 also being isolated from the sterilized parts through the sterile membrane) which comprises a support body 501 with a linear sliding groove, a lead screw 503 is rotatably disposed on the support body 501, the lead screw 503 is sleeved with a sliding block 502 that is threadedly fitted with the lead screw 503 and slidably disposed in the linear sliding groove, one end of the support body 501 is provided with a motor 504, and the output shaft of the motor 504 is securely connected to the lead screw 503 through a coupling. The motor driving unit housing 401 is securely connected to the sliding block 502. When the output shaft of the motor 504 rotates, the sliding block 502 will drives the motor driving unit housing 401 to perform linear movement along the linear sliding groove, so as to implement the feed motion of the flexible surgical instrument 10.

In a preferred embodiment, more than one (one in this embodiment) support ring 108 can also be arranged in the middle connecting body 15, and the structural backbone guide channel 151 and the driving shaft 213 pass through a support ring 108 and function to support the structural backbone guide channel 151 and the driving shaft 213.

Figure 12:
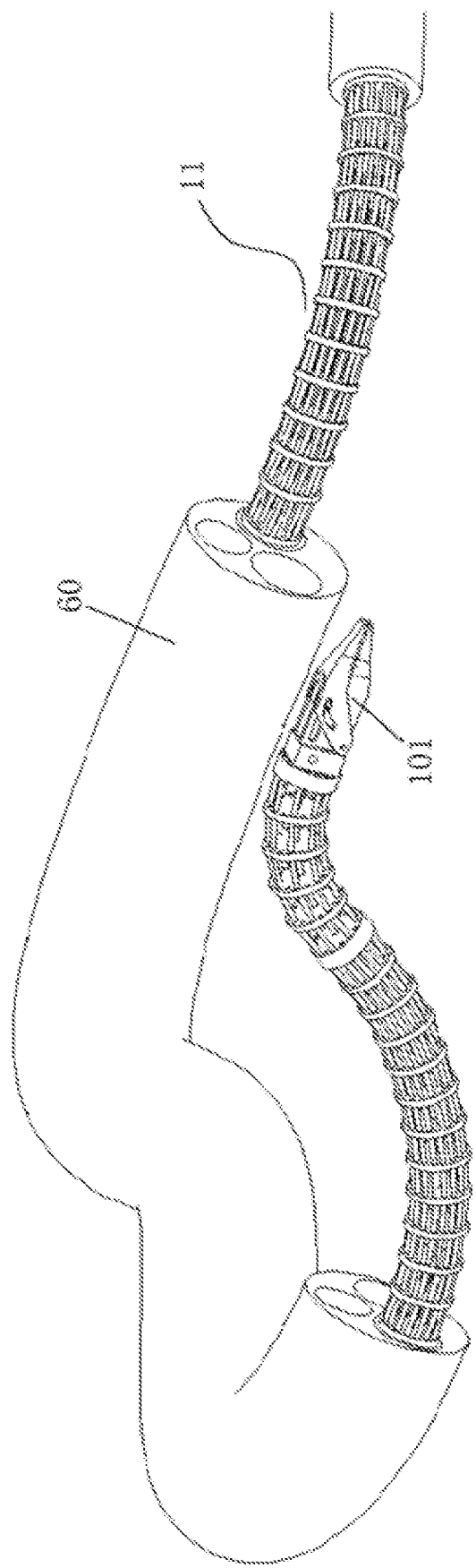
FIG. 12 is a structural schematic diagram of the distal structure of the present invention using a flexible trocar.

In a preferred embodiment, as shown in FIGS. 1 and 12, an envelope 103 is disposed outside the distal structure 11 and functions to improve the smoothness of the distal structure 11 entering a natural orifice or a surgical incision in the human body. An outer sheath 104 and a trocar 60 may also be provided on the outside of the envelope 103. As shown in FIG. 1, in an application, the trocar 60 is fixed at a single incision in the abdominal cavity, and the distal structure 11, together with the envelope 103 and the surgical end effector 101, can freely pass through a through-hole in the trocar 60 for the passage of the surgical instrument and access to the surgical site. As shown in FIG. 12, in another application, the trocar 60 may also be a flexible trocar that can more easily extend into various natural orifices of the human body and adaptively change shape as the shape of the orifices, one end of the flexible trocar is fixed at the entrance of the orifice, and the distal structure 11, together with the envelope 103 and the surgical end effector 101, can freely pass through a through-hole in the flexible trocar for the passage of the surgical instrument and access to the surgical site.

Figure 13:
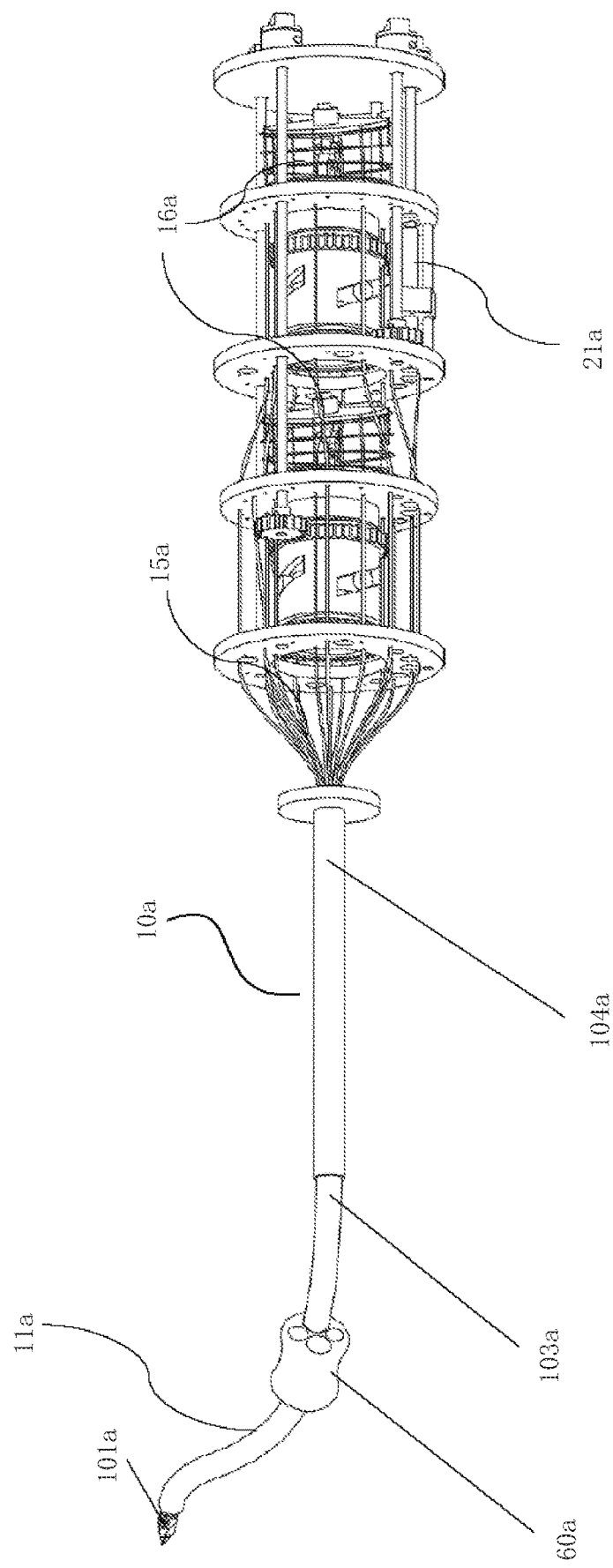
FIG. 13 is an overall structural schematic diagram of a flexible surgical instrument system according to a second embodiment of the present invention.

FIG. 13 illustrates a flexible surgical instrument system 10a according to another embodiment of the present invention, the flexible surgical instrument system comprising a flexible continuum structure consisting of a distal structure 11a, a proximal structure 16a and a middle connecting body 15a, and a transmission driving unit 21a linked to the flexible continuum structure. Here, a proximal end of the distal structure 11a is linked to the proximal structure 16a via the middle connecting body 15a, and a distal end is a surgical effecting end. The transmission driving unit 21a is linked to the proximal structure 16a, and when the transmission driving unit 21a drives the proximal structure 16a to bend or turn in any arbitrary direction, the distal structure 11a correspondingly bends or turns in the opposite direction.

Figure 14:
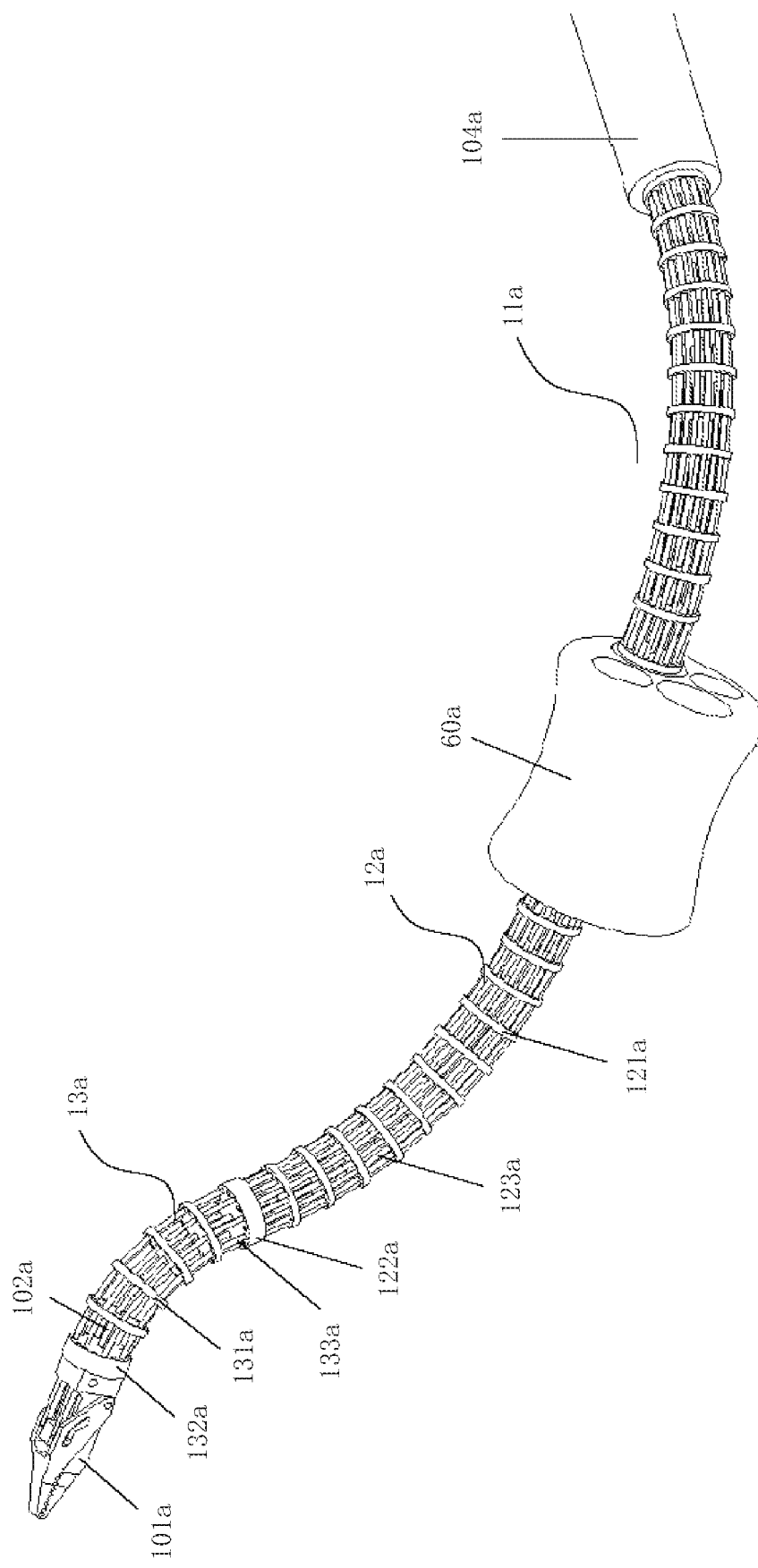
FIG. 14 is a structural schematic diagram of a distal structure in FIG. 13.

As shown in FIG. 14, the distal structure 11a comprises a surgical end effector 101a, a first distal segment 12a and a second distal segment 13a. Here, the first distal segment 12a comprises first distal spacer disks 121a, a first distal fixation disk 122a and first segment structural backbones 123a. A number of first distal spacer disks 121a are distributed in the first distal segment 12a at intervals, and functions to prevent the first segment structural backbones 123a from losing stability when being pushed. A plurality of the first segment structural backbones 123a pass through structural backbone passing holes distributed in the first distal spacer disks 121a, with the tail ends thereof fixed onto the first distal fixation disk 122a. Similarly, the second distal segment 13a comprises second distal spacer disks 131a, a second distal fixation disk 132a and second segment structural backbones 133a. A number of second distal spacer disks 131a are distributed in the second distal segment 13a at intervals, and functions to prevent the second segment structural backbones 133a from losing stability when being pushed. A plurality of the second segment structural backbones 133a pass through structural backbone passing holes distributed in the second distal spacer disks 131a, with the tail ends thereof fixed onto the second distal fixation disk 132a. It should be noted that the first segment structural backbones 123a and the second segment structural backbones 133a should respectively be three or more in number.

Figure 15:
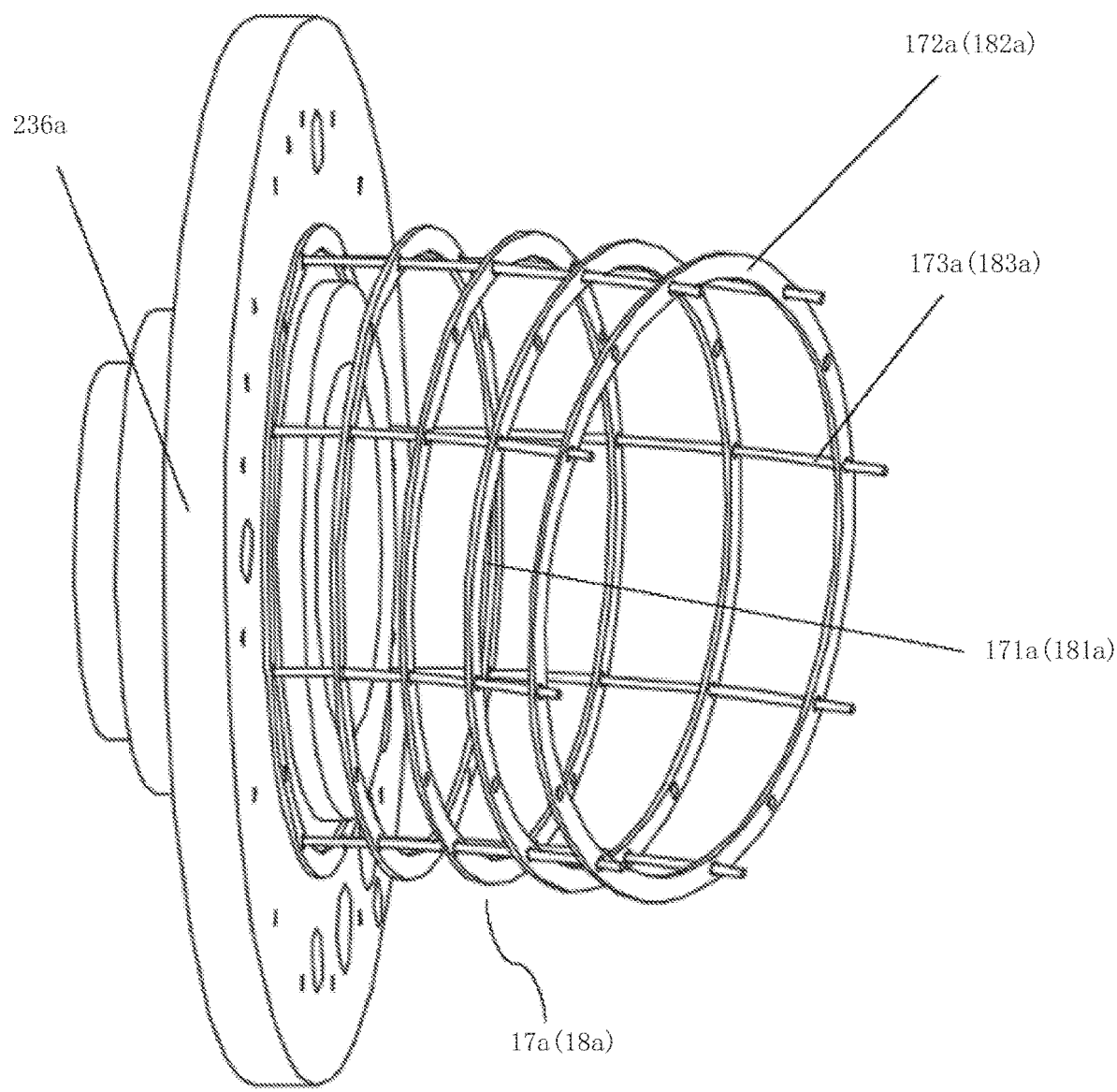
FIG. 15 is a structural schematic diagram of a proximal segment in FIG. 13.

As shown in FIGS. 13 and 15, the proximal structure 16a comprises a first proximal segment 17a and a second proximal segment 18a with identical structures. The first proximal segment 17a comprises first proximal spacer disks 171a, a first proximal fixation disk 172a and first segment structural backbones 173a, and a number of the first proximal spacer disks 171a are distributed in the first proximal segment 17a at intervals and function to prevent the first segment structural backbones 173a from losing stability when being pushed. Similarly, the second proximal segment 18a comprises second proximal spacer disks 181a, a second proximal fixation disk 182a and second segment structural backbones 183a, and a number of the second proximal spacer disks 181a are distributed in the second proximal segment 18a at intervals and function to prevent the second segment structural backbones 183a from losing stability when being pushed. The first segment structural backbones 173a on the first proximal segment 17a are securely connected, in one-to-one correspondence, to or are the same as the first segment structural backbones 123a on the first distal segment 12a; and the second segment structural backbones 183a on the second proximal segment 18a are securely connected, in one-to-one correspondence, to or are the same as the second segment structural backbones 133a on the second distal segment 13a. It should be noted that the first segment structural backbones 173a and the second segment structural backbones 183a should be consistent in number with the first segment structural backbones 123a and the second segment structural backbone 133a, respectively.

Figure 16:
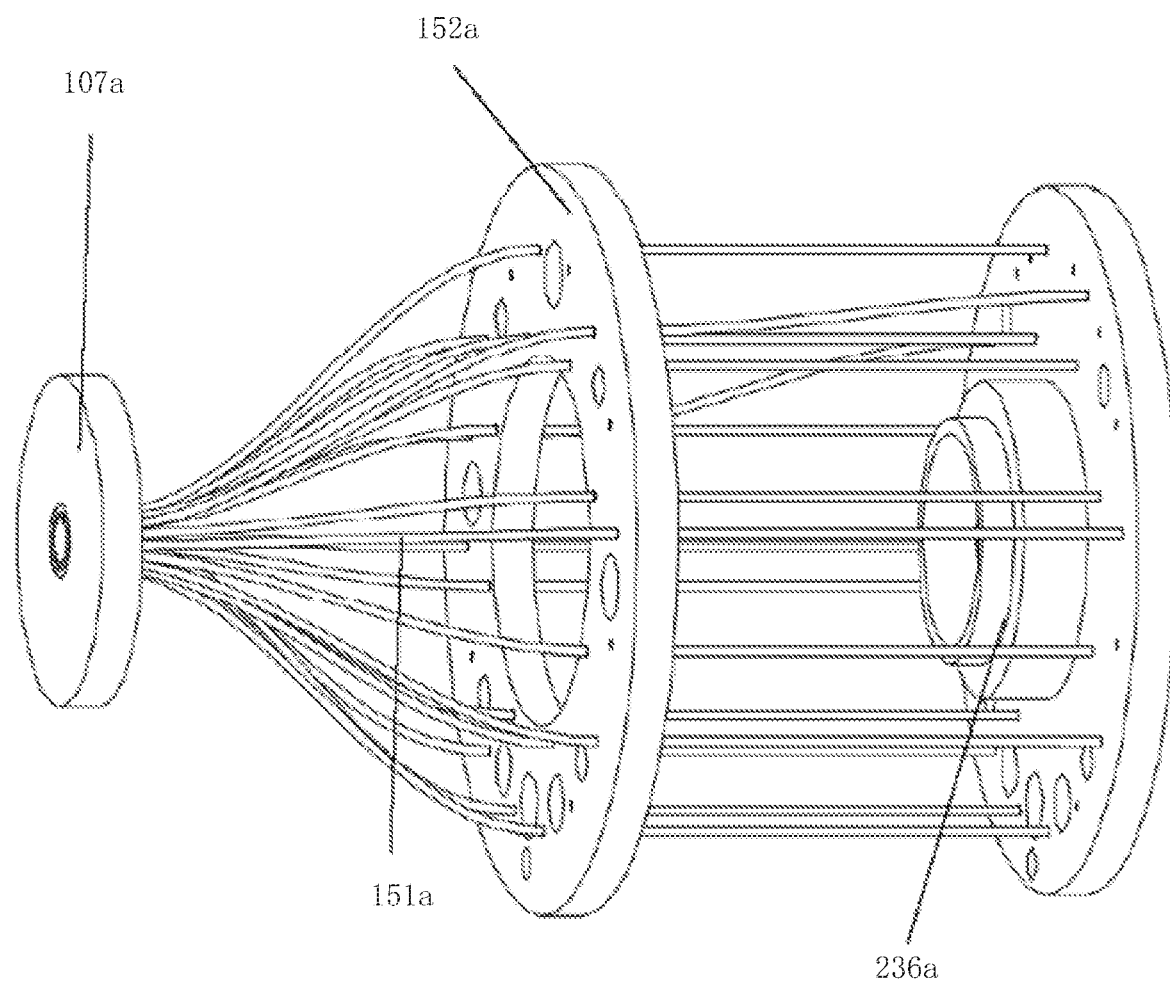
FIG. 16 is a structural schematic diagram of a middle connecting body in FIG. 13.

As shown in FIG. 16, the middle connecting body 15a comprises a flexible surgical instrument distal plate 107a, a channel support plate 152a and a cam transmission mechanism base plate 236a disposed in sequence at intervals, and structural backbone guide channels 151a which have two ends fixedly connected between the flexible surgical instrument distal plate 107a and the cam transmission mechanism base plate 236a and passes through the channel support plate 152a. It should be noted that the channel support plate 152a and the cam transmission mechanism base plate 236a may be provided as one group, or may be provided as multiple groups (for example, two groups are provided in FIG. 17) disposed alternately, and the number of groups of the channel support plate 152a and the cam transmission mechanism base plate 236a is consistent with the number of the cam transmission mechanisms 22a. One end of the first segment structural backbone 173a (123a) is securely connected to the first proximal fixation disk 172a, and the other end passes through the first proximal spacer disks 171a, the structural backbone guide channel 151a and the first distal spacer disks 121a in sequence and is then securely connected to the first distal fixation disk 122a. One end of the second segment structural backbone 183a (133a) is securely connected to the second proximal fixation disk 182a, and the other end passes through the second proximal spacer disks 181a, the structural backbone guide channel 151a, the first distal segment 12a and the second distal spacer disks 131a in sequence and is then securely connected to the second distal fixation disk 132a. The structural backbone guide channel 151a functions to maintain the shape of the structural backbone under a pushing or pulling force. In a preferred embodiment, the above structural backbones in the distal structure 11a and/or the structural backbones in the proximal structure 16a may be elastic thin rods or thin tubes, and are made of a material such as nickel titanium alloy or stainless steel. Meanwhile, the number of the above distal segments in the distal structure 11a and the proximal segments in the proximal structure 16a may be one or more than two. However, the number of the distal segments in the distal structure 11a is consistent with the number of the proximal segments in the proximal structure 16a all the time. In the case of using a plurality of distal segments or proximal segments, if the structural backbone of the former distal segment or proximal segment uses an elastic thin tube, the structural backbone of the next distal segment or proximal segment can pass through the elastic thin tube or directly passes through structural backbone passing holes in the distal spacer disks or the proximal spacer disks, which implements further miniaturization without changing the relative motion relationship in the distal structure 11a or the proximal structure 16a. Moreover, the relative arrangement of the proximal segments in the proximal structure 12a can be series connection, nested arrangement, or independent arrangement (as shown in FIG. 13), etc.

Figure 17:
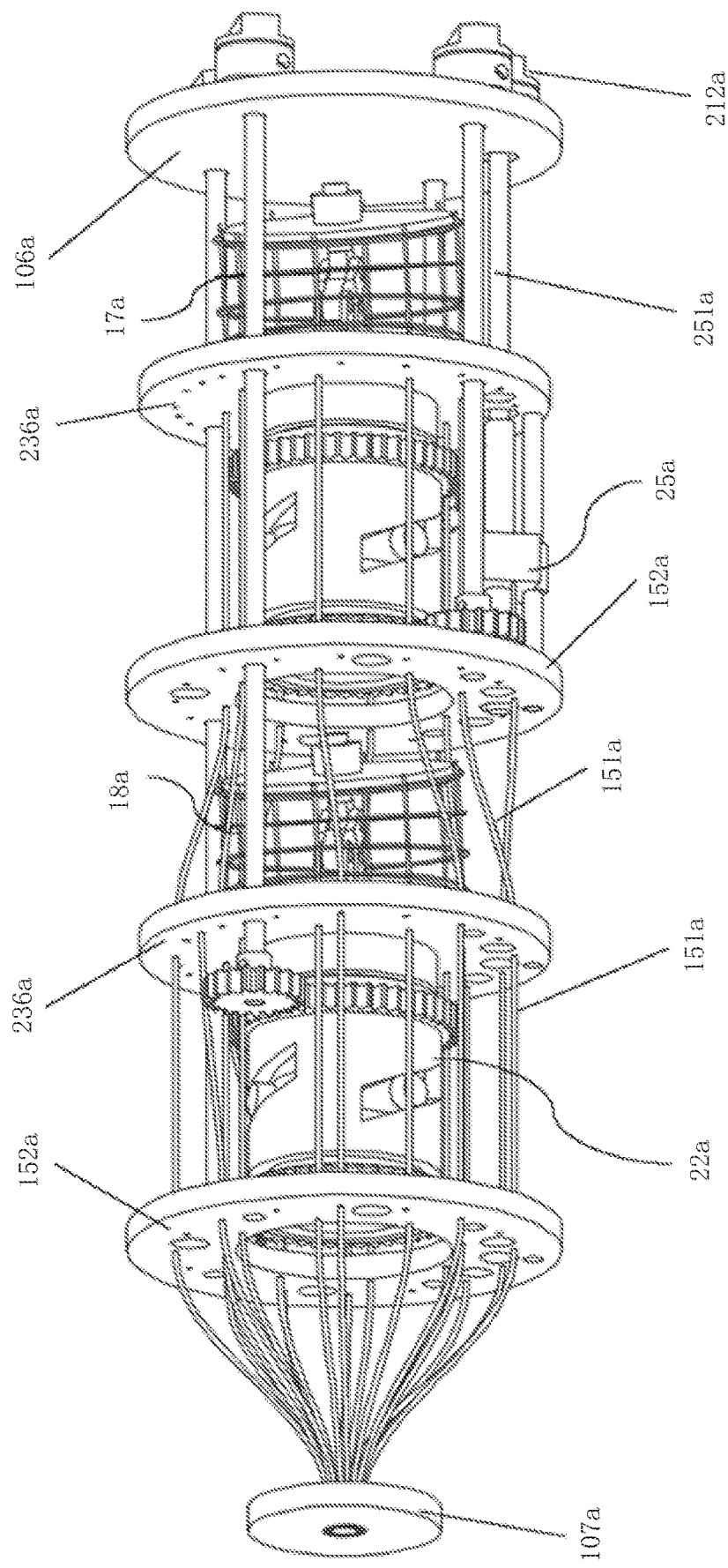
FIG. 17 is a structural schematic diagram of a transmission driving unit in FIG. 13.
Figure 18:
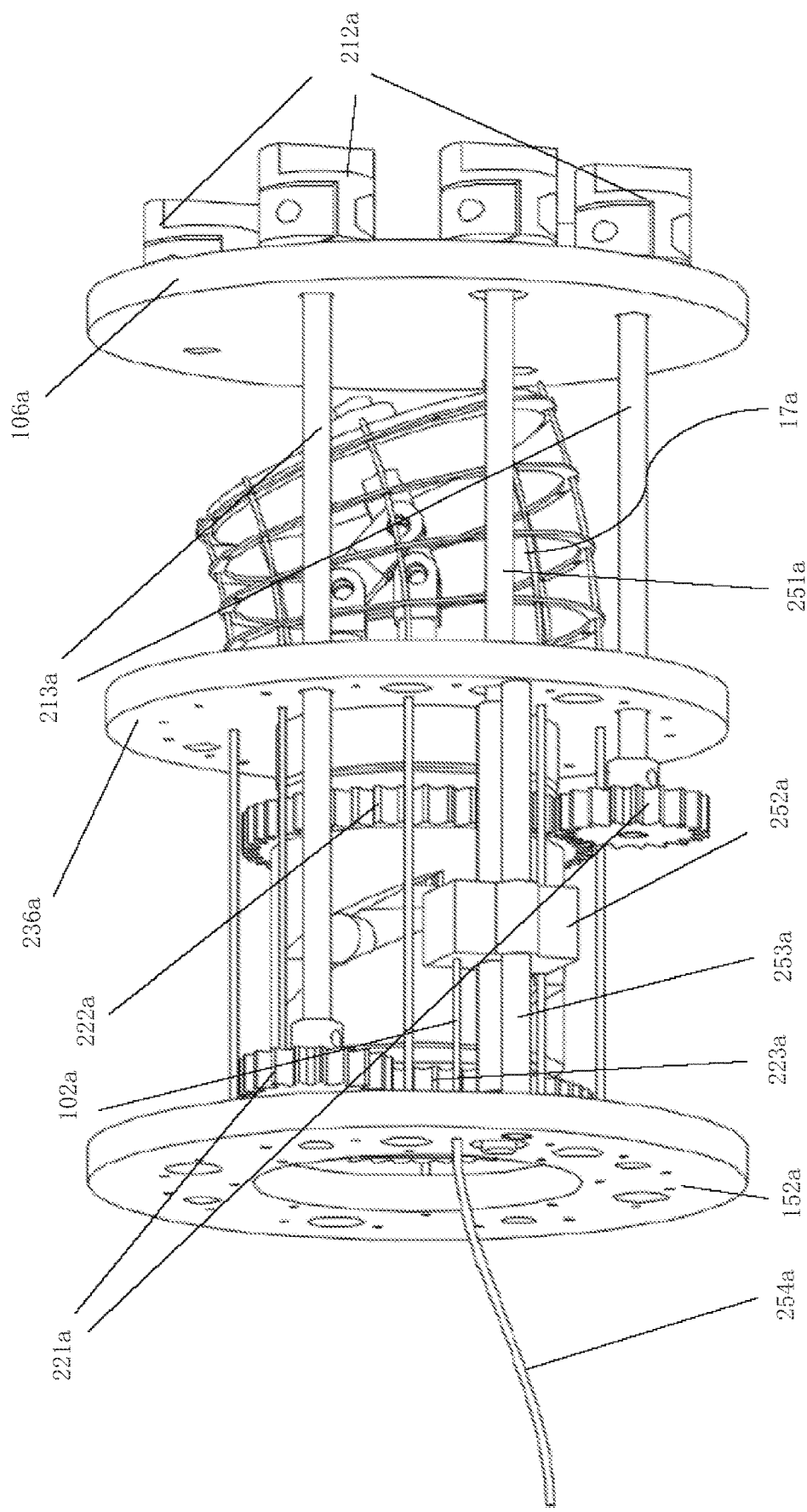
FIG. 18 is a structural schematic diagram of a cam transmission mechanism and a surgical end effector driving mechanism in FIG. 13.
Figure 19:
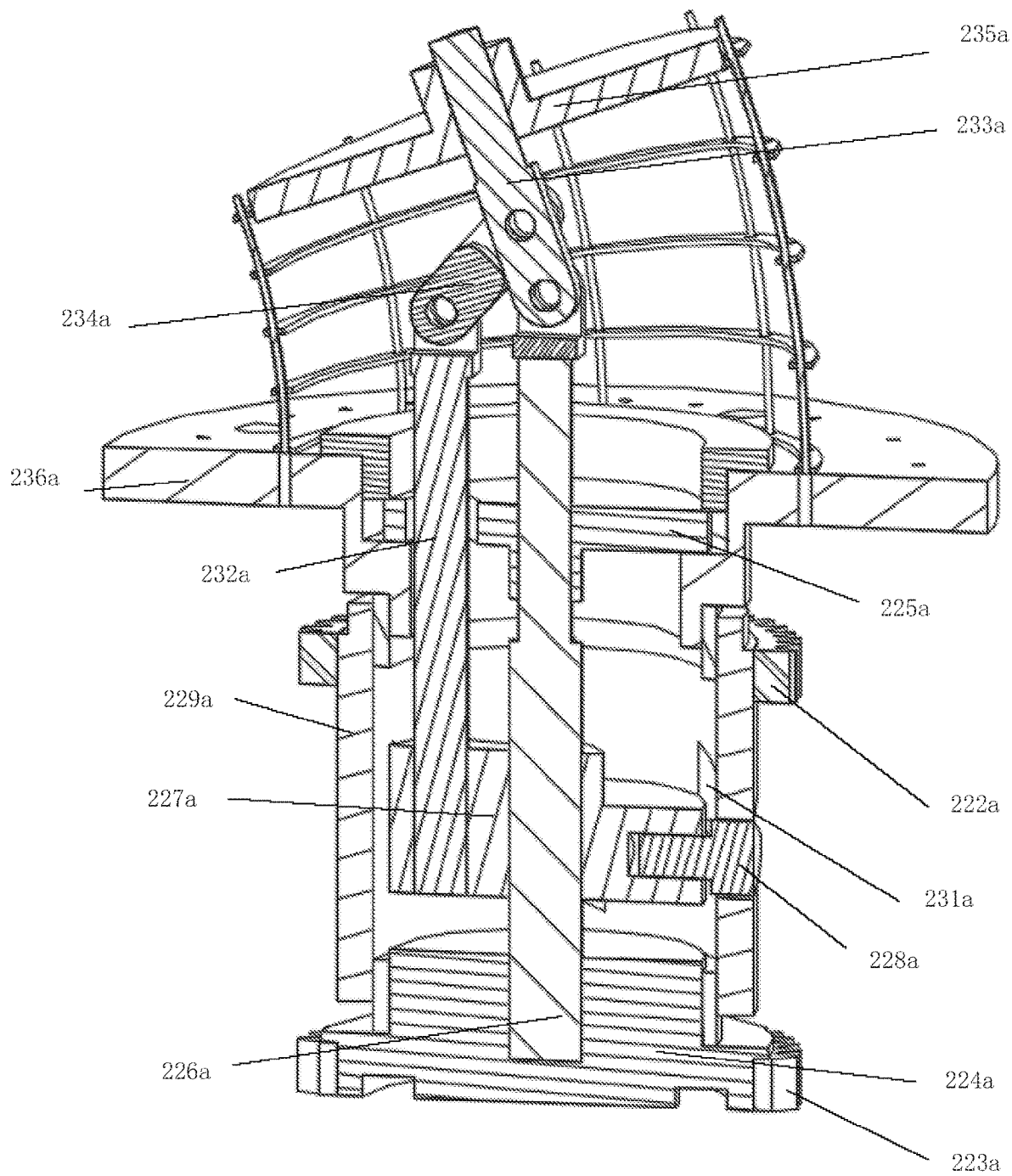
FIG. 19 is a cross-sectional view of a cam transmission mechanism in FIG. 18.

As shown in FIGS. 17 to 19, the transmission driving unit 21a comprises two cam transmission mechanisms 22a (only by way of example, and not limited thereto) correspondingly driving the first proximal segment 17a and the second proximal segment 18a, respectively. The cam transmission mechanism 22a comprises two driving gears 221a securely connected to one end of the two driving shafts 213a, respectively, and the other end of the two driving shafts 213a are coaxially and securely connected to the two coupling male connecters 212a, respectively. The driving gear 221a respectively mesh with a first driven ring gear 222a and a second driven ring gear 223a and drive same to rotate. The first driven ring gear 222a is securely connected to a cam 229a, and the cam 229a is rotatably connected to the cam transmission mechanism base plate 236a; and the second driven ring gear 223a, a transmission shaft 226a, a rotary driving plate 224a and a support plate 225a are securely connected as a whole, the support plate 225a is rotatably connected to the cam transmission mechanism base plate 236a, and the cam 229a is rotatably connected to the rotary driving plate 224a. A sliding block 227a is securely connected to a push rod 232a, and is axially slidably connected to the transmission shaft 226a and can transmit a circumferential rotary motion; and preferably, the sliding block 227a can be connected to the transmission shaft 226a via a ball spline. A number of rollers 228a are securely connected to the sliding block 227a, and the rollers 228a match spiral cam slots 231a on the cam 229a and can generate a push-pull force in the axial direction of the transmission shaft 226a. The push rod 232a is slidably connected to the support plate 225a, and passes through the support plate 225a and is rotatably connected to one end of the connecting rod 234a, and the other end of the connecting rod 234a is rotatably connected to a rocking bar 233a that is rotatably fixed to the transmission shaft 226a; and the rocking bar 233a is slidably connected to a proximal fixation disk driving plate 235a, while both the first proximal fixation disk 172a and the second proximal fixation disk 182a are securely connected to one proximal fixation disk driving plate 235a.

When the driving gear 221a drives the first driven ring gear 222a to rotate, the cam 229a securely connected thereto is driven to rotate, so that the roller 228a is sliding in cam slots 231a; with the spiral cam slot 231a, the roller 228a and the sliding block 227a fixedly connected to the roller 228a as well as the push rod 232a can slide along the transmission shaft 226a, the push rod 232a drives the rocking bar 234a by the connecting rod 233a to oscillate in a certain range, and the rocking bar 233a slides relative to the proximal fixation disk driving plate 235a to drive the proximal fixation disk driving plate 237a to bend or turn so as to directly control the bending angles of the first proximal segment 17a and the second proximal segment 18a in a specific bending plane without changing the lengths of the first proximal segment 17a and the second proximal segment 18a, so that the first proximal segment 17a and the second proximal segment 18a bend or turn in an approximately circular arc shape; and when the second driven ring gear 223a rotates, it drives the rotary driving plate 224a, the transmission shaft 226a and the support plate 225a securely connected thereto, and drives the sliding block 227a via the transmission shaft 226a to perform a rotary motion together, and a planar linkage mechanism consisting of the push rod 232a, the connecting rod 233a and the rocking bar 234a rotates therewith, so as to finally change the direction of the bending planes of the first proximal segment 17a and the second proximal segment 18a. In the first driving mode, when the first driven ring gear 222a and the second driven ring gear 223a are driven to rotate in the same direction at the same angular speed, the sliding block 227a is stationary relative to the cam 229a, the roller 228a does not relatively slide in the cam slot 231a, and thus the sliding block 227a and the push rod 232a have no sliding motion in the axial direction, and at this moment the bending angles of the first proximal segment 17a and the second proximal segment 18a in the respective bending planes remain unchanged, only having a change in the direction of the bending plane; and in the second driving mode, the first driven ring gear 222a is driven while the second driven ring gear 223a remains stationary, at this moment the cam 229a rotates relative to the sliding block 227a, the transmission shaft 226a remains stationary and limit rotation of the sliding block, the roller 228a slides back and forth in the cam slot 231a in the axial direction of the transmission shaft 226a, and thus the sliding block 227a drives the push rod 232a securely connected thereto to axially slide, and at this moment the direction of the bending planes of the first proximal segment 17a and the second proximal segment 18a remain unchanged, only with the change in the bending angle in the bending plane. Combining the first driving mode with the second driving mode, cooperative control for the direction of the bending plane and for the bending angle in the bending plane of the first proximal segment 17a and the second proximal segment 18a can be implemented. When the first proximal segment 17a bends or turns in a certain direction, the first distal segment 12a will bend or turn in the opposite direction in a certain proportional relationship (determined by the distribution radius of the first segment structural backbone 123a (173a) together); and similarly, when the second proximal segment 18a bends or turns in a certain direction, the second distal segment 13a will bend or turn in the opposite direction in a certain proportional relationship (determined by the distribution radius of the second segment structural backbone 133a (183a) together).

In a preferred embodiment, the distal end of the distal structure 11a is provided with a surgical end effector 101a (as shown in FIGS. 13 and 14), one end of a surgical end effector control line 102a is securely connected to the surgical end effector 101a, and the other end thereof passes through the distal structure 11a and is connected to a surgical end effector driving mechanism 25a (as shown in FIGS. 17 and 18) at a tail end of the transmission driving unit 21a, so that the surgical end effector driving mechanism 25a implements the motion control for the mechanical surgical end effector 101a (such as a surgical clamp, etc.) by physically pushing and pulling the surgical end effector control line 102a. It will be understood by those skilled in the art that the surgical end effector control line 102a can also transmit energy, such as electric energy, ultrasonic vibration, etc., to an electrosurgical surgical end effector 101a (such as an electric knife, an ultrasonic knife, etc.) so as to implement the specific surgical function of the surgical end effector 101a. The surgical end effector driving mechanism 25a comprises a threaded rod 251a and a nut 252a. Here, the threaded rod 251a is rotatably supported between the channel support plate 152a and a flexible surgical instrument bottom plate 106a, one end of the threaded rod 251a is coaxially and securely connected to another coupling male connecter 212a, the threaded rod 251a is threadedly fitted with the nut 252a, and a guide rod 253a is securely connected between the cam transmission mechanism base plate 236a and the channel support plate 152a and is slidably connected to the nut 252a. The threaded rod 251a is driven to rotate by the coupling male connecter 212a, so that the nut 252a is guided by the guide rod 253a to move back and forth in linear motion to push and pull the surgical end effector control line 102a which has one end securely connected to the nut 252a, so as to finally implement the motion control for the surgical end effector 101a.

Figure 20:
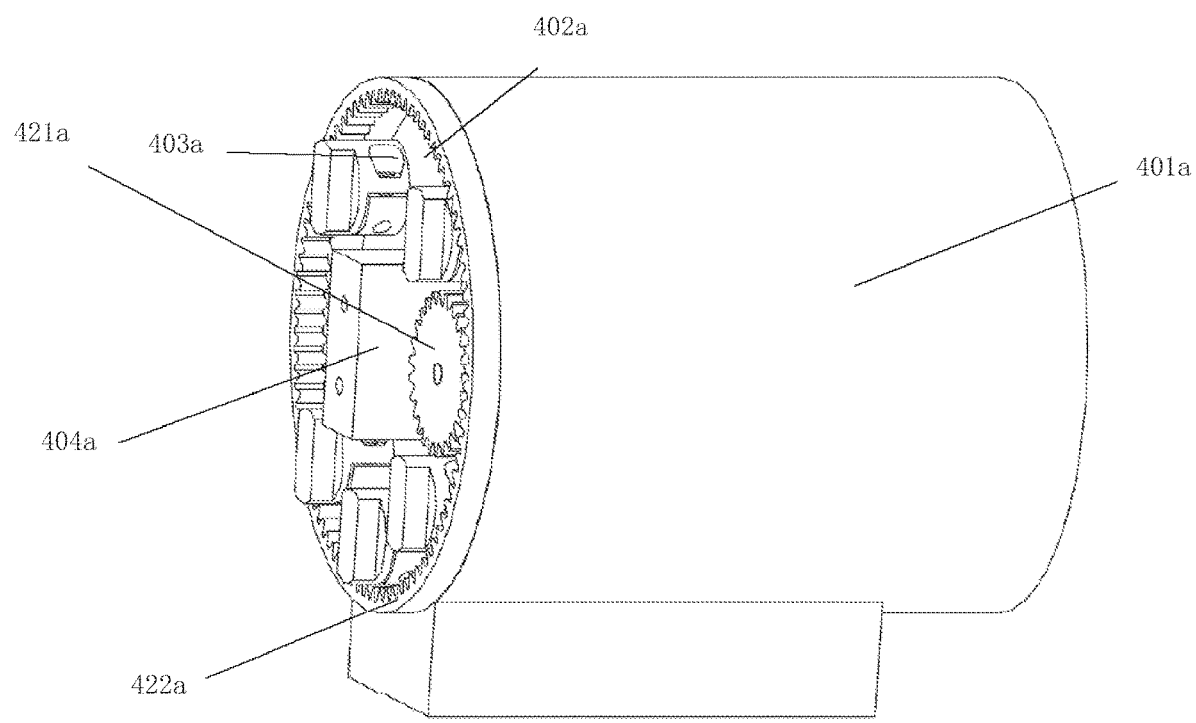
FIG. 20 is a structural schematic diagram of a motor driving unit of the flexible surgical instrument system according to the second embodiment of the present invention.
Figure 21:
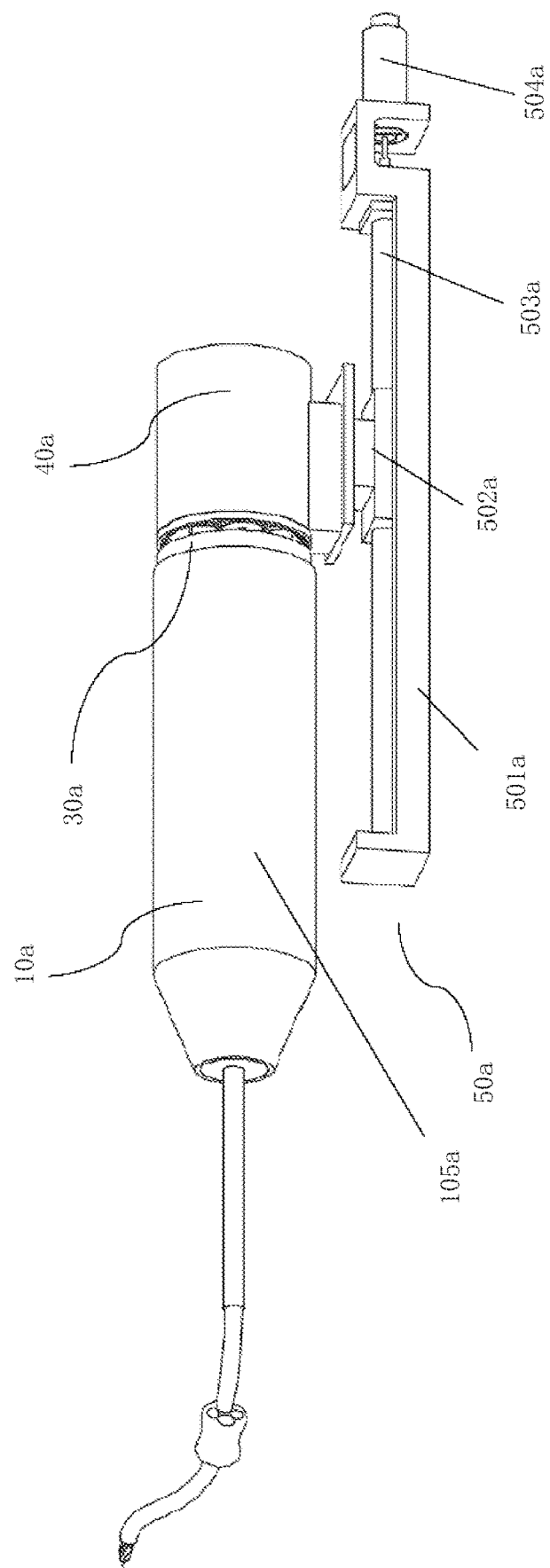
FIG. 21 is a schematic diagram of a structure installed with a sterile barrier, a motor driving unit and a linear module according to the second embodiment of the present invention.

In a preferred embodiment, as shown in FIGS. 20 and 21, the present invention further comprises a motor driving unit 40a linked to the flexible surgical instrument 10a, and the motor driving unit 40a comprises a motor driving unit housing 401a, a motor fixation plate 402a, a gear 421a and an inner ring gear 422a. Here, the motor driving unit housing 401a is located at the periphery of the motor fixation plate 402a, an end surface of the motor driving unit housing 401a is securely connected to the inner ring gear 422a, and the motor fixation plate 402 a is rotatably connected to the motor driving unit housing 401a. A plurality of motors (six motors in this embodiment) are securely connected to the motor fixation plate 402a, in which the output shaft of one of the motors is securely connected to the gear 421a, the output shafts of the remaining motors are securely connected to coupling male connecters 403a, and the gear 421a meshes with the inner ring gear 422a. The motor connected to the gear 421a can drive the gear 421a to rotate, and drive all the structures, other than the motor driving unit housing 401*a* and the inner ring gear 422*a*, in the motor driving unit 40*a* to rotate as a whole around the axis of the inner ring gear 422*a* so as to achieve control over the roll angle of the distal structure 11*a* and the surgical end effector 101*a*.

In this embodiment, the linear module (see FIG. 10), the sterile barrier (see FIG. 11) and the flexible trocar (see FIG. 12) of the first embodiment may also be used.

In a preferred embodiment, as shown in FIGS. 11 and 21, the flexible surgical instrument 10*a* can be quickly connected to the motor driving unit 40*a* via a sterile barrier 30, the sterile barrier 30 comprises a sterile barrier cover 301 and a sterile barrier support plate 302, and the sterile barrier support plate 302 is rotatably provided with a plurality of coupling female connecters 303 that can be quickly coupled with the coupling male connecters 212*a* and 403*a*. A motor driving unit connecting screw 304 is provided on the sterile barrier support plate 302, and correspondingly, a sterile barrier connecting base 404*a* (as shown in FIG. 20) is provided on the motor fixation plate 402*a*, and the sterile barrier connecting base 404*a* can be quickly connected to the motor driving unit connecting screw 304, so that the sterile barrier 30 can be fixedly connected to the motor fixation plate 402*a* and can transmit an overall movement. A sterile membrane (not shown in the figure) is securely connected on the sterile barrier cover 301 to isolate the sterilizable parts (such as the flexible surgical instrument 10*a* and other parts in front of the sterile barrier 30) from the unsterilized parts (such as the motor driving unit 40*a*, a linear module 50*a* and other parts behind the sterile barrier 30) to ensure the clinical practicability of the surgery.

In a preferred embodiment, as shown in FIG. 21, the present invention further comprises a linear module 50*a* (the linear module 50*a* also being isolated from the sterilized parts through the sterile membrane) which comprises a support body 501*a* with a linear sliding groove, a lead screw 503*a* is rotatably disposed on the support body 501*a*, the lead screw 503*a* is sleeved with a sliding block 502*a* that is threadedly fitted with the lead screw 503*a* and slidably disposed in the linear sliding groove, one end of the support body 501*a* is provided with a motor 504*a*, and the output shaft of the motor 504*a* is securely connected to the lead screw 503*a* through a coupling. The motor driving unit housing 401*a* is securely connected to the sliding block 502*a*. When the output shaft of the motor 504*a* rotates, the sliding block 502*a* will drives the motor driving unit housing 401*a* to perform linear movement along the linear sliding groove, so as to implement the feed motion of the flexible surgical instrument 10*a*.

The present invention has been illustrated only by the above embodiments, and the structure, arrangement position and connection of the components can be varied. On the basis of the technical solutions of the present invention, the improvements or equivalent changes to individual components according to the principles of the present invention should not be excluded from the scope of protection of the present invention.

The invention claimed is:

1. A surgical instrument, comprising:
   a distal structure comprising at least one distal structural segment, the at least one distal structural segment comprising a distal fixation disk and distal structural backbones;
   a proximal structure comprising at least one proximal structural segment, the at least one proximal structural segment comprising a proximal fixation disk and proximal structural backbones, the distal structural backbones being securely connected to or the same as corresponding proximal structural backbones; and
   a transmission driving unit comprising a transmission mechanism operable to control direction of a bending plane of the at least one proximal segment and control bending angle of the at least one proximal segment,
   wherein the transmission mechanism comprises:
      a proximal fixation disk driving plate securely connected to the proximal fixation disk;
      a direction control part operable to rotate the proximal fixation disk driving plate around a first axis to control the direction of the bending plane of the at least one proximal segment; and
      a bending transmission part operable to turn the proximal fixation disk driving plate to control the bending angle of the at least one proximal segment,
   the transmission mechanism further comprises:
      a support base operable to receive a first rotation motion;
      an oscillating shaft support securely connected to the support base; and
      a guide column slidably connected to the proximal fixation disk driving plate and rotatably connected to the oscillating shaft support, and
      the bending transmission part operable to receive a second rotation motion to rotate the guide column around a second axis to turn the proximal fixation disk driving plate, or
   the transmission mechanism further comprises:
      a rotary driving plate operable to receive a first rotation motion;
      a transmission shaft securely connected to the rotary driving plate; and
      a rocking bar slidably connected to the proximal fixation disk driving plate and rotatably connected to the transmission shaft, and
      the bending transmission part is operable to receive a second rotation motion to rotate the rocking bar around a second axis to turn the proximal fixation disk driving plate.

2. The surgical instrument of claim 1, wherein the bending transmission part comprises:
   a planetary gear transmission shaft operable to receive the second rotation motion;
   a planetary bevel gear securely connected to the planetary gear transmission shaft; and
   an oscillation bevel gear operable to rotate the guide column around the second axis and in meshing with the planetary bevel gear.

3. The surgical instrument of claim 2, wherein the bending transmission part further comprises:
   an oscillating shaft coaxially with the second axis and rotatably disposed on the oscillating shaft support; and
   a web plate securely connected to the oscillating shaft, and
   the oscillation bevel gear and the guide column are securely connected to the web plate.

4. The surgical instrument of claim 3, wherein:
   the transmission mechanism further comprises:
      a first driven gear operable to receive the first rotation motion and disposed at edge of the support base, and
   the bending transmission part further comprises:
      a planetary gear securely connected to the planetary gear transmission shaft; and
      a second driven gear operable to receive the second rotation motion and in meshing with the planetary gear.

5. The surgical instrument of claim 1, wherein the bending transmission part comprises:
   a cam comprising a spiral cam slot;
   a sliding block comprising a roller slidably connected in the spiral cam slot and operable to form a linear motion of the sliding block; and
   a planar linkage mechanism comprising a first end securely connected to the sliding block and a second end connected to the rocking bar.

6. The surgical instrument of claim 5, wherein the planar linkage mechanism comprises:
   a push rod securely connected to the sliding block; and
   a connecting rod comprising a first connecting end and a second connecting end rotatably connected to the push rod and the rocking bar, respectively.

7. The surgical instrument of claim 6, wherein:
   the transmission mechanism further comprises:
      a first driven gear to receive the first rotation motion and disposed at edge of the rotary driving plate;
   the bending transmission part further comprises:
      a second driven gear to receive the second rotation motion and disposed at edge of the cam.

8. The surgical instrument of claim 1, wherein a proximal end of the proximal structural backbone is securely connected to the proximal fixation disk, and a distal end of the distal structural backbone is securely connected to the distal fixation disk.

9. The surgical instrument of claim 1, wherein:
   the at least one proximal structural segment further comprises a proximal spacer disk, the proximal structural backbone passing through the proximal spacer disk; and
   the at least one distal structural segment further comprises a distal spacer disk, the distal structural backbone passing through the distal spacer disk.

10. The surgical instrument of claim 9, wherein:
    the distal structure comprises a plurality of the distal structural segments or the proximal structure comprises a plurality of the proximal structural segments,
    the distal structural backbones of a preceding distal structural segment or the proximal structural backbones of a preceding proximal structural segment comprises elastic tubes, the distal structural backbones of a next distal structural segment or the proximal structural backbones of a next proximal structural segment are able to pass through the elastic tubes or directly pass through structural backbone passage holes in the distal spacer disk or in the proximal spacer disk, respectively.

11. The surgical instrument of claim 1, further comprising a middle connecting body comprising:
    a distal channel fixation plate close to the at least one distal structural body;
    a base plate close to the at least one proximal structural body; and
    structural backbone guide channels disposed between the distal channel fixation plate and the base plate, and
    the distal structural backbone passes through the structural backbone guide channel and a distal end of the distal structural backbone is securely connected to the distal fixation disk.

12. The surgical instrument of claim 1, further comprising:
    a surgical end effector disposed at a distal end of the distal structure;
    a surgical end effector control line passing through the distal structure, the surgical end effector control line comprising a proximal end securely connected to a surgical end effector driving mechanism and a distal end securely connected to the surgical end effector.

13. A surgical instrument system, comprising:
    a surgical instrument comprising:
       a distal structure comprising at least one distal structural segment, the at least one distal structural segment comprising a distal fixation disk and distal structural backbones;
       a proximal structure comprising at least one proximal structural segment, the at least one proximal structural segment comprising a proximal fixation disk and proximal structural backbones, the distal structural backbones being securely connected to or the same as corresponding proximal structural backbones; and
       a transmission driving unit comprising a transmission mechanism operable to control direction of a bending plane of the at least one proximal segment and control bending angle of the at least one proximal segment; and
    a motor driving unit operable to drive the transmission driving unit,
    wherein the transmission mechanism comprises:
       a proximal fixation disk driving plate securely connected to the proximal fixation disk;
       a direction control part operable to rotate the proximal fixation disk driving plate around a first axis to control the direction of the bending plane of the at least one proximal segment; and
       a bending transmission part operable to turn the proximal fixation disk driving plate to control the bending angle of the at least one proximal segment,
    the transmission mechanism further comprises:
       a support base operable to receive a first rotation motion;
       an oscillating shaft support securely connected to the support base; and
       a guide column slidably connected to the proximal fixation disk driving plate and rotatably connected to the oscillating shaft support, and
       the bending transmission part operable to receive a second rotation motion to rotate the guide column around a second axis to turn the proximal fixation disk driving plate, or
    the transmission mechanism further comprises:
       a rotary driving plate operable to receive a first rotation motion;
       a transmission shaft securely connected to the rotary driving plate; and
       a rocking bar slidably connected to the proximal fixation disk driving plate and rotatably connected to the transmission shaft, and
       the bending transmission part is operable to receive a second rotation motion to rotate the rocking bar around a second axis to turn the proximal fixation disk driving plate.

14. The surgical instrument system of claim 13, wherein the motor driving unit comprises:
    a motor driving unit housing;
    a motor fixation plate rotatably connected to inside of the motor driving unit housing; and
    a plurality of first motors securely connected to the motor fixation plate.

15. The surgical instrument system of claim 14, wherein the motor driving unit further comprises:
    an inner ring gear securely connected to an end surface of the motor driving unit housing; and a gear securely connected to one of the first motors and meshing with the inner ring gear.

16. The surgical instrument system of claim 15, further comprising a sterile barrier disposed between the surgical instrument and the motor driving unit and comprising:
   a sterile barrier cover;
   a sterile barrier support plate securely connected to the motor fixation plate and disposed inside the sterile barrier cover; and
   a plurality of couplings rotatably disposed in the sterile barrier support plate.

17. The surgical instrument system of claim 13, further comprising:
   a linear module to drive the surgical instrument and the motor driving unit to perform a linear motion.

* * * * *